(12) United States Patent
Zhang et al.

(10) Patent No.: US 11,202,585 B2
(45) Date of Patent: Dec. 21, 2021

(54) MULTI-CARRIER NONCONTACT SIGNAL DETECTION WITH NOISE SUPPRESSION BASED ON A PHASE-LOCKED LOOP

(71) Applicant: Georgia Tech Research Corporation, Atlanta, GA (US)

(72) Inventors: Ying Zhang, Atlanta, GA (US); Zongyang Xia, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 650 days.

(21) Appl. No.: 16/060,781

(22) PCT Filed: Dec. 9, 2016

(86) PCT No.: PCT/US2016/065871
§ 371 (c)(1),
(2) Date: Jun. 8, 2018

(87) PCT Pub. No.: WO2017/100605
PCT Pub. Date: Jun. 15, 2017

(65) Prior Publication Data
US 2018/0368739 A1    Dec. 27, 2018

Related U.S. Application Data

(60) Provisional application No. 62/265,446, filed on Dec. 10, 2015.

(51) Int. Cl.
*A61B 5/113*    (2006.01)
*A61B 5/00*    (2006.01)
(Continued)

(52) U.S. Cl.
CPC ............ *A61B 5/1135* (2013.01); *A61B 5/024* (2013.01); *A61B 5/0205* (2013.01);
(Continued)

(58) Field of Classification Search
CPC ... A61B 5/0204; A61B 5/0507; A61B 5/7203; A61B 5/7228; A61B 5/024
See application file for complete search history.

(56) References Cited

U.S. PATENT DOCUMENTS

| | | |
|---|---|---|
| 2010/0130873 A1 | 5/2010 | Yuen et al. |
| 2010/0198083 A1 | 8/2010 | Lin et al. |

(Continued)

OTHER PUBLICATIONS

Search Report and Opinion from PCT Application No. PCT/US16/31939 dated Aug. 16, 2016 (21 pages).

*Primary Examiner* — Puya Agahi
(74) *Attorney, Agent, or Firm* — Troutman Pepper Hamilton Sanders LLP; Ryan A. Schneider

(57) ABSTRACT

In one aspect, embodiments of the present disclosure can comprise a non-contact signal detection system for detecting movement associated with a subject. The system can comprise a carrier source configured to generate a first carrier signal in phase coherence with a second carrier signal. Additionally, the system may incorporate a phase-locked loop including noise pre-cancellation system for suppressing the noise associated with a beat signal and a controlled oscillation system. The noise pre-cancellation system can be configured to phase-lock the beat signal to a first reference signal in order to stabilize the phase of the beat signal and pre-cancel the noise associated with the beat signal. The controlled oscillation system can include a propagation pathway on which a transmission signal is phase-modulated with a vibratory signal of the subject. Once acquired, the vibratory signal can have suppressed noise.

14 Claims, 14 Drawing Sheets

(51) Int. Cl.
  *A61B 5/0205*  (2006.01)
  *A61B 5/024*  (2006.01)
  *A61B 5/0507*  (2021.01)
  *A61B 5/08*  (2006.01)

(52) U.S. Cl.
  CPC .......... *A61B 5/0507* (2013.01); *A61B 5/0816* (2013.01); *A61B 5/7203* (2013.01); *A61B 5/7228* (2013.01)

(56) References Cited

U.S. PATENT DOCUMENTS

2013/0030257 A1     1/2013   Nakata et al.
2016/0336989 A1*   11/2016   Lin ..................... H04L 27/3881

* cited by examiner

MULTI-CARRIER NONCONTACT SIGNAL DETECTION WITH NOISE SUPPRESSION BASED ON A PHASE-LOCKED LOOP

CROSS-REFERENCE TO RELATED APPLICATIONS

This application is a U.S. National Stage Entry of PCT/US2016/065871, filed on Dec. 9, 2016, which claims the benefit of U.S. Provisional Patent Application No. 62/265,446, filed Dec. 10, 2015, which is hereby incorporated by reference herein in its entirety as if fully set forth below.

BACKGROUND

There has been a growing interest in developing noncontact vital sign detection systems due to their promising applications in the field of biomedical monitoring, health care, physical monitoring for astronauts, and search and rescue after mudslides or earthquakes. Various wireless solutions have been developed for vital sign detection using the stepped-frequency continuous wave (SFCW), the frequency modulated continuous wave (FMCW), the Doppler radar, and the impulse-based ultrawideband radar. SFCW, FMCW, and impulse-based radar provide flexibility in controlling the frequency band to meet the application requirement on the band and resolution, and provide both distance and image information. However, they pose high requirements on the frequency chirp linearity and bandwidth to accurately detect small displacements in sub-millimeters and even millimeters. Thus, to realize the detection of vital signs in millimeters, these solutions place a critical demand on the linearity and bandwidth of detecting waves, which requires a complex subsystem to achieve. The Continuous Wave (CW) Doppler radar uses the frequency or phase shift in the reflected radar signal to detect physiological movements. It can reach a resolution of sub-millimeters and is suitable for vital sign detection, including detection of the respiration and heartbeat of a subject.

Vital sign detection through Doppler radar is based on phase modulation of the reflected signal at the surface of the human chest. Chest displacement due to heartbeat and respiration is exhibited in the phase variation of microwave signals, and a larger displacement causes a more obvious phase variation. For instance, for human beings at rest, the chest displacement caused by respiration and heartbeat is typically 4-12 mm and 0.2-0.5 mm, respectively. Therefore, the respiration signal has a stronger power spectrum density than the heartbeat signal in Doppler detection. As the vital sign is contained in the phase of microwave signals, phase noise of the received signal has a significant influence on the vital sign detection. For instance, it can raise the background noise floor, deteriorate the performance of the signal, and impair the signal-to-noise ratio (SNR), which can decrease the detection accuracy and distance. Residual phase noise, which increases with detection distance as well as the oscillator phase noise level, exists in almost all detection environments, while the transmission path noise is associated with the surroundings and is especially notable in applications with complex environments, such as search and rescue after earthquakes.

It is with respect to these and other considerations that the various aspects of the disclosed technology as described below are presented.

SUMMARY

Aspects of the present disclosure relate to systems and methods for non-contact signal detection of movement associated with a subject.

Some aspects of the present disclosure relate to a non-contact signal detection system for detecting movement associated with a subject. In some embodiments, the system can include a carrier source configured to generate a first carrier signal in phase coherence with a second carrier signal. In some embodiments, to establish phase coherence, the carrier source can be phase-locked to a second reference signal generated by a reference oscillator. The system can also include a noise pre-cancellation system for suppressing a phase noise and a path noise associated with a beat signal. The noise pre-cancellation system can be configured to phase-lock the beat signal to a first reference signal to stabilize the phase of the beat signal. In some embodiments, the first reference signal can be generated by a low noise reference oscillator.

In some embodiments, the noise pre-cancellation system can comprise a phase-frequency detector, a low-pass filter, and a voltage controlled oscillator (VCO). The phase-frequency detector can be in communication with the low-pass filter and a demodulator and configured to receive the beat signal from the demodulator and the first reference signal. The phase-frequency detector can discriminate the beat signal with the reference signal and transmit a phase control signal. In some embodiments, the phase-frequency detector and low-pass filter can control the phase of the VCO, such that when the VCO is in communication with the phase-frequency detector and low-pass filter it can receive the phase control signal and transmit a noise pre-cancelled signal.

The system can also comprise a controlled oscillation system. The noise pre-cancellation system can be in communication with a controlled oscillation system. In some embodiments, the controlled oscillation system can comprise a modulator in communication with the noise pre-cancellation system and the carrier source. The modulator can be configured to frequency-modulate the first carrier signal and the second carrier signal with the noise pre-cancelled signal and transmit a transmission signal to a propagation pathway. In some embodiments, the transmission signal can comprise both the frequency-modulated first carrier and frequency-modulated second carrier. In some aspects, the propagation pathway can provide a pathway through which the transmission signal is wirelessly transmitted to the subject. In some embodiments, the subject may be moving in some way and generate a vibratory signal associated with that movement. Through the propagation pathway, the transmission signal can come in contact with the vibratory signal and the vibratory signal can phase-modulate the transmission signal to create a reflected signal. In some embodiments, the first carrier signal and the second carrier signal can also be phase-modulated by the vibratory signal associated with the subject. Through the propagation pathway, the reflected signal can be received by the demodulator.

In some embodiments, the controlled oscillation system can comprise a demodulator. The demodulator can be in communication with the propagation pathway, the carrier source, and the noise pre-cancellation system. The demodulator can be configured to receive the reflected signal from the propagation pathway and the second carrier from the carrier source, and transmit the beat signal to the noise pre-cancellation system. The demodulator can be configured to extract a beat signal from the reflected signal. In some embodiments, the demodulator can be in communication with a data acquisition device configured to acquire information associated with the movement of the subject for data analysis from the beat signal.

In some embodiments, the transmission signal can be transmitted to a third branch in communication with and between the modulator and the demodulator to provide auxiliary feedback to the demodulator. In some embodiments, the vibratory signal can be associated with a vital sign of the subject.

Embodiments of the present disclosure can also include a dual-carrier source configured to generate a first carrier signal in phase coherence with a second carrier signal and a phase-locked loop in communication with the dual-carrier source. The phase-locked loop can comprise a phase-frequency detector, a low-pass filter, and a VCO. The phase-frequency detector can be configured to phase-lock a beat signal to a first reference signal and transmit a phase control signal. Additionally, the VCO can be configured to receive the phase control signal, suppress the noise associated with the beat signal, and transmit a noise pre-cancelled signal. The noise pre-cancelled signal can then be received by the controlled oscillation system, as described previously.

Embodiments of the present disclosure can include a method for detecting movement associated with a subject. The method can comprise generating, by a carrier source, a first carrier signal in phase coherence with a second carrier signal. In some embodiments, the generating, by the carrier source, can comprise phase-locking the first carrier signal and the second carrier signal with a second reference signal generated by a reference oscillator. The method can also include using a noise pre-cancellation system for suppressing a phase noise and a path noise of a beat signal by phase-locking the beat signal to a first reference signal to stabilize the phase of the beat signal. Additionally, the noise pre-cancellation system can be used for transmitting the noise pre-cancelled signal. The method can also comprise using a modulator in communication with the noise pre-cancellation system and the carrier source for frequency-modulating the first carrier signal and the second carrier signal with the noise pre-cancelled signal. Then, the modulator can transmit a transmission signal. The transmission signal from the demodulator can be transmitted to the subject through a propagation pathway. From the propagation pathway, a reflected signal can be received, wherein the reflected signal includes the transmission signal phase-modulated with a vibratory signal associated with movement of the subject. The reflected signal and the second carrier signal can be received by a demodulator in communication with the carrier source and the noise pre-cancellation system, and the beat signal can be transmitted to the noise pre-cancellation system.

In some embodiments, when suppressing the phase noise and the path noise of the beat signal by phase-locking the beat signal to a first reference signal to stabilize the phase of the beat signal, the phase frequency detector can receive the beat signal and the first reference signal and transmit a phase control signal. The VCO may then receive the phase control signal from the phase frequency detector and pre-cancel the noise associated with the beat signal.

In some embodiments, the method can also comprise extracting, from the reflected signal, i) information associated with the vibratory signal of the subject, and ii) the beat signal, and the extracting can be performed by the demodulator. In one embodiment, the vibratory signal can be associated with a vital sign of the subject.

In one embodiment, the method can comprise providing auxiliary feedback to the demodulator by transmitting the transmission signal to a third branch, the third branch in communication with and between the modulator and the demodulator.

Embodiments of the present disclosure can also comprise a non-contact signal detection method. The method can include generating a first carrier signal in phase coherence with a second carrier signal; providing a beat signal. The method can include phase-locking the beat signal to a first reference signal to stabilize the phase of the beat signal. Then, the method an include suppressing a phase noise and a path noise of the beat signal to produce a noise pre-cancelled signal. Using the noise pre-cancelled signal, the method can include frequency-modulating the first carrier signal and the second carrier signal with the noise pre-cancelled signal to produce a transmission signal. Then the transmitted signal can be wirelessly transmitted to the subject through a propagation pathway. Through the propagation pathway, the transmission signal can be phase-modulated with a vibratory signal associated with the movement of the subject, to produce a reflected signal. Then, the reflected signal can be received. Following, the method can include extracting, from the reflected signal, i) information associated with the vibratory signal of the subject, and ii) the beat signal.

Other aspects and features according to the example embodiments of the disclosed technology will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

DETAILED DESCRIPTION

Figure 1A:
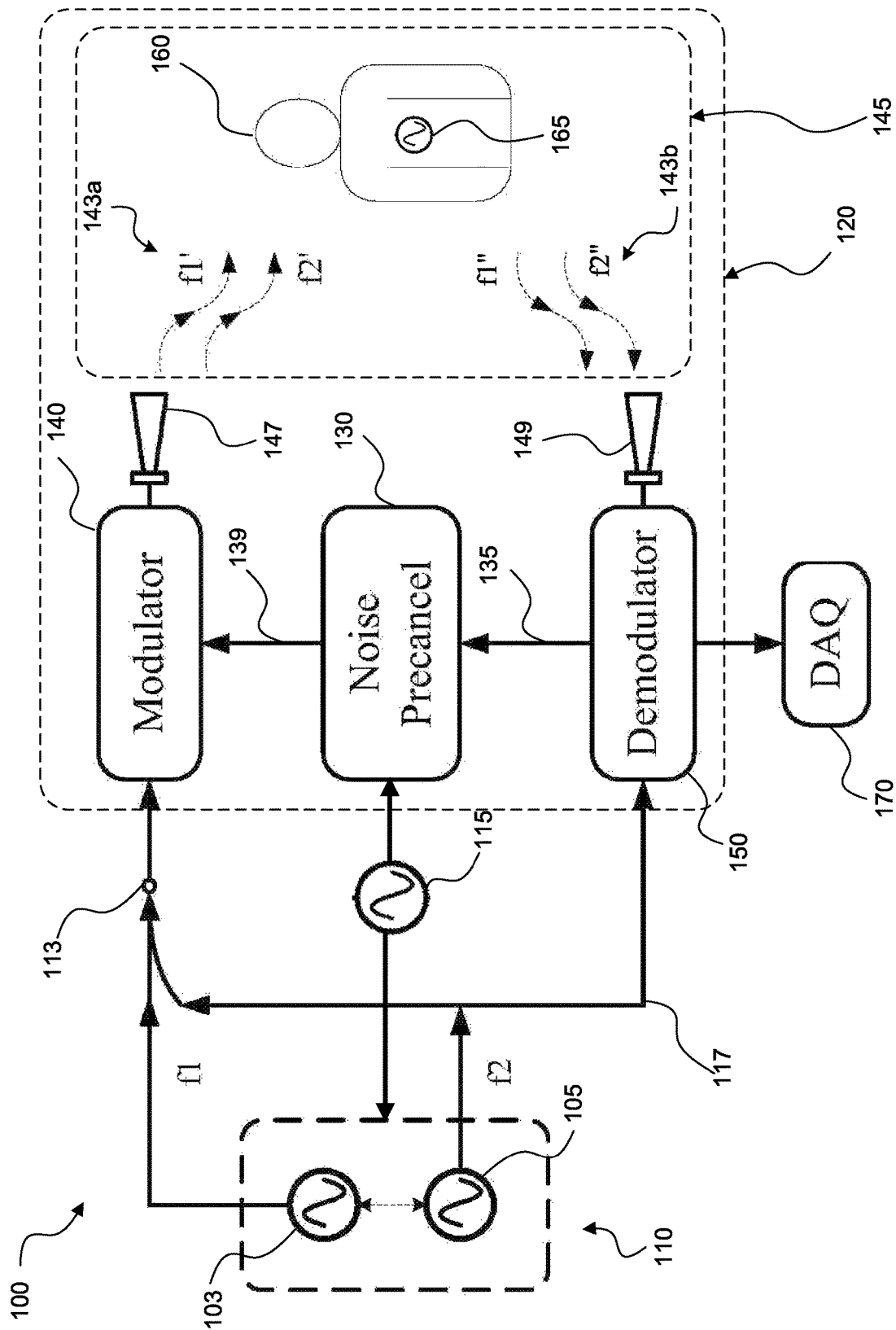
FIG. 1a illustrates a non-contact signal detection system, in accordance with one embodiment of the present disclosure.

In some aspects, the present disclosure relates to non-contact, signal detection of movement associated with a subject. Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

A detailed description of aspects of the present disclosure, in accordance with various example embodiments, will now be provided with reference to the accompanying drawings. The drawings form a part hereof and show, by way of illustration, specific embodiments and examples. In referring to the drawings, like numerals represent like elements throughout the several figures.

Embodiments of the present disclosure can comprise a non-contact signal detection system that can suppress the residual phase noise and transmission path noise, associated with a signal. Carrier waves can be transmitted to a subject and phase-modulated by a vibratory signal associated with movement of the subject, received, and analyzed. As the reflected signal is transmitted along this path, the signal may be particularly susceptible to broadband waves due to environmental factors that can increase the path noise and phase noise associated with the signal. This increase in noise can make it particularly challenging to extract a meaningful signal. Embodiments of the present disclosure can reduce the effects of phase and path noise by incorporating a multi-carrier system and a phase-locked loop for pre-canceling noise and thereby improving the quality of vibratory signal detection. For instance, in some embodiments using a phase-locked loop design, the system can automatically adjust the transmitted signals to suppress this noise even when the noise changes during signal detection. By incorporating a phase-locked loop design, a beat signal can be phase-locked to a reference signal provided by a low-noise oscillator and the phase-locked loop can control the phase of a voltage controlled oscillator (VCO). Thus, the residual phase noise and path noise can be pre-cancelled and the vital sign signal can be recovered with relatively low noise.

FIG. 1a illustrates a non-contact signal detection system 100 for detecting movement associated with a subject 160, in accordance with an embodiment of the presently disclosed technology. As shown, the non-contact signal detection system 100 comprises a carrier source 110 configured to generate a first carrier signal 103 and a second carrier signal 105. The first carrier signal 103 can comprise a signal-extraction carrier, and the second carrier signal 105 can comprise a noise-suppression carrier. The signal-extraction carrier can include a carrier from which a vibratory signal 165 from a subject 160 is carried and extracted. The noise-suppression carrier can include a carrier transmitted to a phase-locked loop 120 and from which noise is extracted and suppressed when the noise-suppression carrier proceeds through the phase-locked loop. The signal-extraction carrier and the noise-suppression carrier can be defined by a first signal at a first frequency (f1) and a second signal at a second frequency (f2), respectively. Additionally, the signal-extraction carrier and the noise-suppression carrier may be in phase coherence. As understood by those skilled in the art, phase coherence can mean the noise-suppression carrier and the signal-extraction carrier have a constant phase difference. As such, the two carriers in phase coherence can propagate through the same path during detection, be influenced by the same level of phase noise, and their phase noises can be pre-cancelled at the same time by a single pre-canceling signal. In some embodiments, phase coherence can be established by phase-locking the carrier source 110 to a reference signal 115 or another appropriate reference signal.

As shown, the disclosed non-contact, signal detection system 100 comprises a phase-locked loop 120. The phase-locked loop 120 is in communication with the carrier source 110 through a first branch 113 and a second branch 117 and the reference signal 115. The first branch 113 can comprise the first carrier signal 103 (i.e., the signal-extraction carrier) power-combined with the second carrier signal 105 (i.e., the noise-suppression carrier). The second branch 117 can comprise the second carrier signal 105.

The phase-locked loop 120 can comprise a noise pre-cancellation system 130 and a controlled oscillation system. The noise pre-cancellation system 130 can be configured to receive a reference signal 115 and a beat signal 135 and lock the beat signal 135 to the reference signal 115. The beat signal 135 can comprise the noise-suppression carrier modulated by the vibratory signal of the subject and frequency demodulated at the demodulator. In other words, the beat signal 135 can be transmitted by the demodulator 150. In some embodiments, the reference signal 115 can be generated by a high-quality, low-noise reference oscillator. The reference oscillator may comprise any commercially available, high-quality oscillator, for instance, a temperature-controlled oscillator or a Rubidium clock. As illustrated, in some embodiments, the reference signal 115 in communication with the noise pre-cancellation system 130 can be the same reference signal 115 as that in communication with the carrier source 110.

Figure 1B:
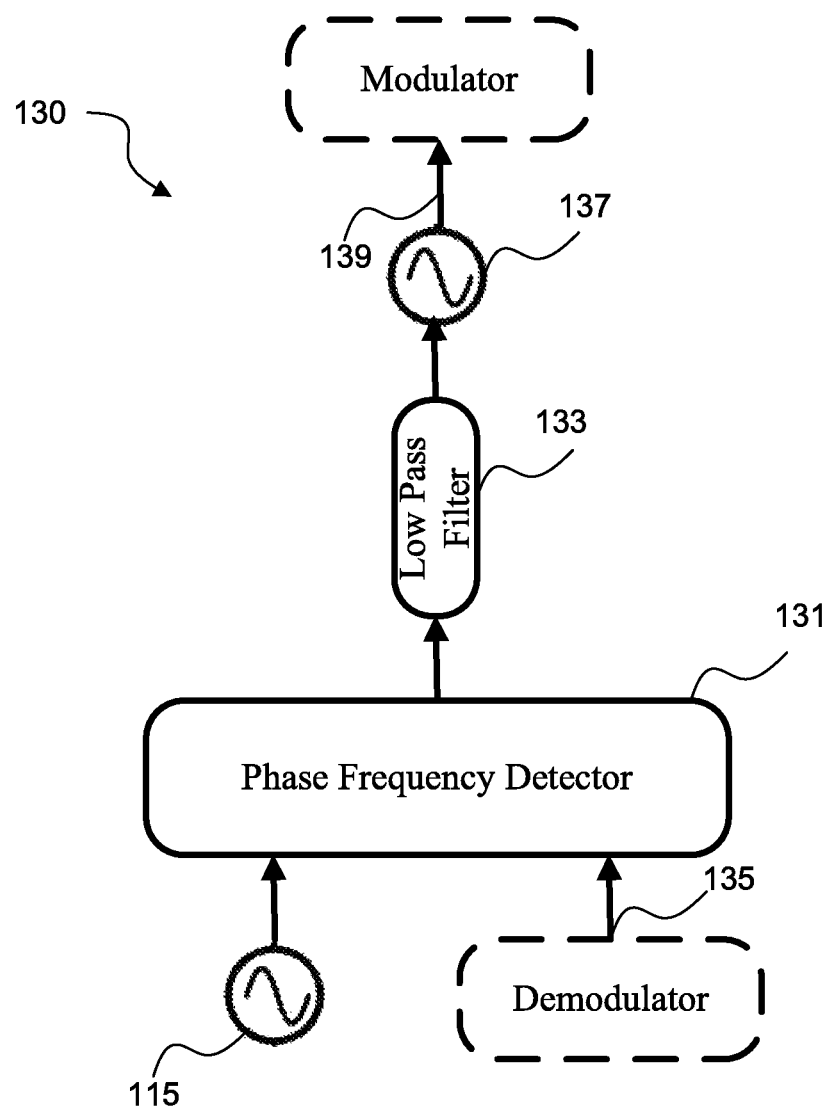
FIG. 1b illustrates a noise pre-cancellation system, in accordance with one embodiment of the present disclosure.

The noise pre-cancellation system 130 can be configured to cancel the noise associated with the beat signal 135, such that the beat signal 135 has a low phase noise (such as residual phase noise) and a low path noise. For instance, in some embodiments, as illustrated at FIG. 1b, the noise pre-cancelling component can comprise a voltage controlled oscillator (VCO) 137. The VCO 137 can cancel the noise associated with the beat signal 135, such that the beat signal 135 contains no information about the subject's vibratory signal 165 and yet the beat signal 135 demonstrates a low phase noise and low path noise. Therefore, the VCO 137 can be configured to generate a noise pre-cancelled signal that can be introduced to the controlled oscillation system.

The controlled oscillation system can comprise a modulator 140, a propagation pathway 145, and a demodulator 150. The modulator 140 can be in communication with the noise pre-cancellation system 130 and a first branch 113. Specifically, the modulator 140 can be in communication with the VCO 137 of the noise pre-cancellation system 130, as illustrated at FIG. 1b. As discussed previously, the first branch 113 can comprise the first carrier 103 power-combined with the second carrier 105. Thus, the modulator 140 can be configured to receive the noise pre-cancelled signal 139 from the noise pre-cancelling component 130, the first carrier signal 103, and the second carrier signal 105. Additionally, the modulator can be configured to frequency-modulate the first carrier signal 103 and the second carrier signal 105 with the noise pre-cancelled signal 139.

The modulator 140 can be configured to output the transmission signal 143a, which can be transmitted to the propagation pathway 145. The transmission signal 143a can be considered the result of the frequency modulation of the first carrier signal 103 (f1') and the second carrier signal 105 (f2') with the noise pre-cancelled signal 139. The propagation pathway 145 can be a transmission pathway through which the transmission signal 143a is wirelessly transmitted to the subject 160. Once the transmission signal 143a comes in contact with a surface of the subject 160, the transmission signal 143a can be phase-modulated with a vibratory signal 165 associated with a movement of the subject 160. The product of this phase modulation is that a reflected signal 143b contains within its phase, information about the vibratory signal 165. The reflected signal 143b can therefore comprise the transmission signal 143a phase-modulated with the vibratory signal 165 of the subject 160, and can be received by the demodulator 150 of the controlled oscillation system.

The demodulator 150 can be configured to receive the reflected signal 143b from the propagation pathway 145. The reflected signal 143b can be carried by both the first carrier signal 103 and the second carrier signal 105, each carrier signal having been frequency-modulated (f1' and f2') with the noise pre-cancelled signal 139 by the modulator 140 phase-modulated by the vibratory signal 165 of the subject 160 (f1" and f2"). The demodulator can also be in communication with a second branch 117 that is coupled with the carrier source 110 and includes only the second carrier signal 105. The demodulator 150 can demodulate the first carrier signal 103, extract the vibratory signal information, and transmit it to the data acquisition device (DAQ) 170. The DAQ 170 can receive the information about the vibratory signal 165 and can be configured to provide information corresponding to the vibratory signal 165. Additionally, the demodulator 150 can be in communication with the noise pre-cancellation system 130 and transmit the beat signal 135 carried by the second carrier signal 105 to the noise pre-cancellation system 130 to lock the loop 120.

Having a carrier source 110 with two or more carriers can be advantageous as it allows for effective long-distance detection as well as noise-suppression without also suppressing the detected vibratory signal 165. Without a carrier source generating two or more carriers, a phase-locked loop would result in suppression of the vibratory signal as well as the noise associated with it. As will be understood, the second carrier signal 105 can travel through the propagation pathway 145 and the phase-locked loop 120 while the first carrier signal 103 will only travel through the propagation path 145. The beat signal 135 received by the noise pre-cancellation device 130 can then be noise-suppressed independent of any information related to the vibratory signal 165, which can be concurrently received at the DAQ 170. The vibratory signal 165 received by the DAQ 170 may be further processed for extracting additional information or parameters associated with the vibratory signal. When the beat signal 135 is transmitted through the noise pre-cancellation system 130, the vibratory signal information can be treated as path noise and suppressed as well.

While the above-described non-contact signal detection system is described as having two carriers, it is understood that the non-contact signal detection system can comprise more than two carriers. Additionally, the first and second frequencies of the first carrier and the second carrier can be adjusted as desired. In some embodiments, the frequencies of the two carriers can be on a microwave frequency scale, having a frequency anywhere between 300 MHz and 300 GHz. In other embodiments, the frequencies of the two carriers can be on a radio frequency scale, having a frequency anywhere between 3 Hz to 300 GHz. As will be understood, the frequency of the carrier signals can be increased, according to different applications.

Additionally, in some embodiments, phase-coherence can be established between the signal-extraction carrier and the noise-suppression carrier. As discussed above, phase coherence can be established by phase-locking the first carrier signal 103 and the second carrier signal 105 to a reference signal 115. In some embodiments, the reference signal can be the same reference signal 115 locked to the phase-locked loop 120, as illustrated at FIG. 1, and in other embodiments, the reference signal may be a low-quality oscillator. As will be understood by those skilled in the art, the carrier signals 103 and 105 need not be locked to a high-quality reference signal as the residual phase noise will be suppressed in the phase-locked loop 120.

An exemplary and non-limiting embodiment of the noise pre-cancellation system 130 is illustrated at FIG. 1b. The noise pre-cancellation system 130 may comprise a phase-frequency detector 131, a low-pass filter 133, and the VCO 137. In some embodiments, the phase-frequency detector 131 can be configured to receive the reference signal 115 and the beat signal 135. The phase-frequency detector 131 can be configured to lock the beat signal 135 to the reference signal 115. The phase frequency detector 131 can be in communication with the low-pass filter 133, which can in turn be in communication with the VCO 137. In some embodiments, the noise pre-cancellation system 130 can instead comprise a phase detector or phase comparator.

In some embodiments, the transmission signal 143a can be transferred to the subject 160 via a TX antenna 147 and the phase-modulated carrier signal can be received by an RX antenna 149. As used herein, a "subject" may be any applicable living or non-living subject. Alternatively, the subject may be living and be a human, an animal, a plant, or other organism. For instance, the subject may be non-living and created by man, such as a bridge, building, or other structure, or is a non-living product of nature. In some embodiments, the subject 160 may be a living subject. For instance, the subject 160 may be a human being and the vibratory signal 165 may comprise information associated with a vital sign, such as a heart beat or respiration of the subject. The displacement of a subject's chest, for instance, can create a low-frequency signal that can modulate the transmission signal, such that the transmission signal will carry the vital sign information in its phase. Therefore, the vital sign information may be extracted at the demodulator 150 and received by the DAQ 170. While embodiments of the present disclosure may be described in terms of a non-contact, signal detection system associated with vibratory signals of a living subject, it will be appreciated that embodiments of the present disclosure may be used to detect other vibratory signals. For instance, the device may be applicable to detecting vibratory signals in structures, such as bridges or buildings.

Figure 2:
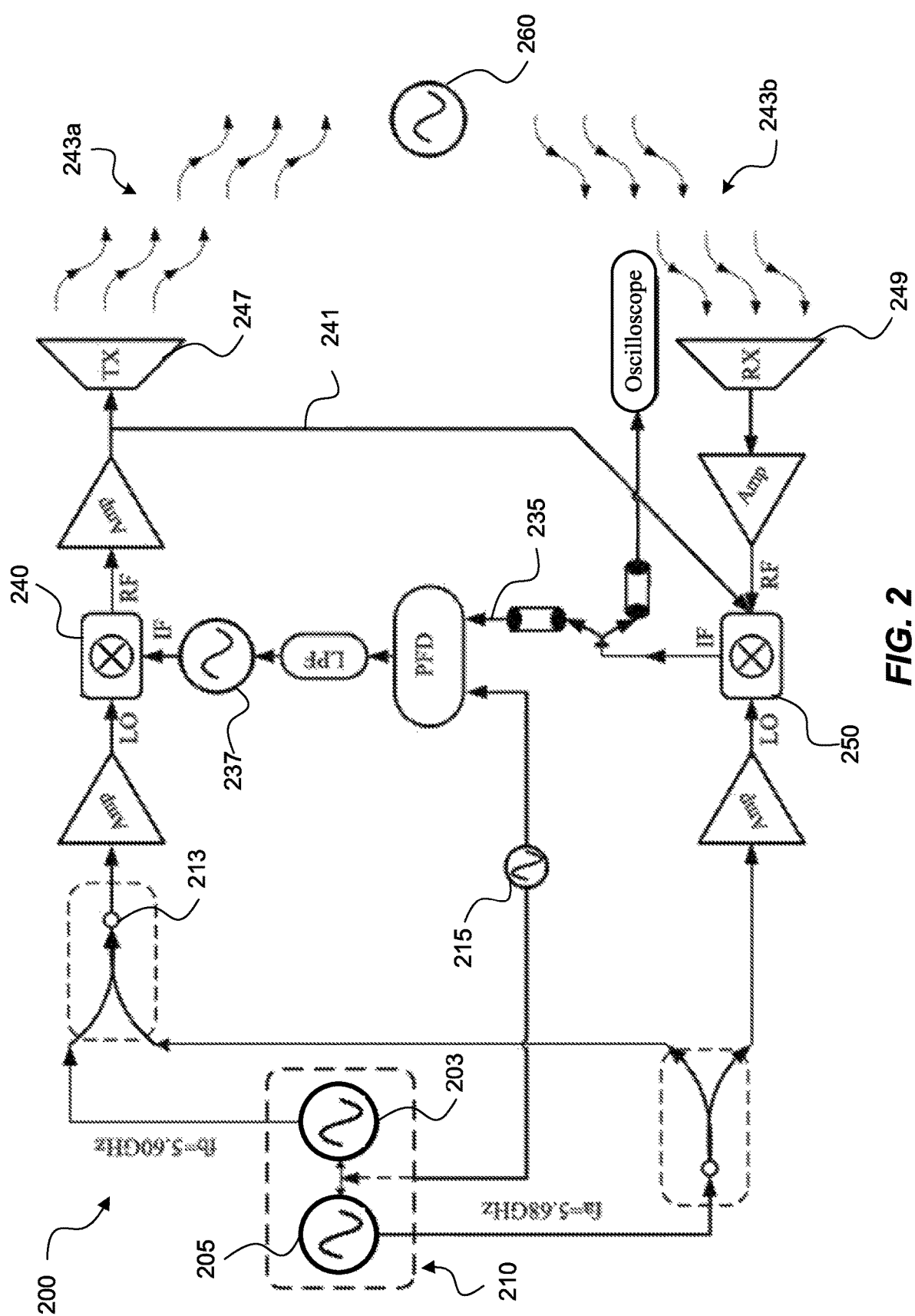
FIG. 2 illustrates a dual-carrier, non-contact signal detection system, in accordance with one embodiment of the present disclosure.

Embodiments of the non-contact signal detection system can be used to detect vibratory signals from a subject at a variety of distances. For instance, in one embodiment, a non-contact signal detection system can be used for measuring a vibratory signal of a subject at distances including 50 cm, 100 cm, 150 cm, 150 cm, 200 cm, 250 cm, and 300 cm, without adjusting the power of the system. In embodiments where the distance is increased, the phase-locked loop 120 may comprise an additional feedback signal, as illustrated at FIG. 2, providing an adequate power to lock the loop. For instance, in an embodiment, the feedback signal can be power combined with the received signal, which the demodulator can receive as an input. In alternative embodiments, the measurement distance may be further increased by adjusting the power, the carrier frequencies, the antenna design, and/or other appropriate components and/or parameters of the system.

Additionally, in some embodiments the demodulator 150 can be an I/Q demodulator. An I/Q demodulator can be advantageous because it can acquire a signal independent of where the subject is located. For instance, the I/Q demodulator can cancel a null point associated with the signal detection. As will be understood, a null point in signal detection will inhibit signal detection of a subject at particular positions. I/Q demodulators can be advantageous as they can cancel the null point by phase-shifting the detected signal by 90 degrees, allowing for detection of a subject at any position with respect to the data acquisition device.

As will be understood, embodiments of the present disclosure can include various other electrical components for otherwise adjusting the system, including one or more amplifiers, one or more low-pass filters, and/or one or more bandwidth filters.

EXAMPLE IMPLEMENTATIONS AND RESULTS

Various aspects of the disclosed technology may be still more fully understood from the following description of example implementations and corresponding results and the images of FIGS. 3-10*d*. Some experimental data are presented herein for purposes of illustration and should not be construed as limiting the scope of the disclosed technology in any way or excluding any alternative or additional embodiments.

Noise Suppression Design Scheme

The efficacy of a described non-contact signal detection system was tested by incorporating one or more aspects of the present disclosure in a non-contact vital sign detection system 200 comprising a dual-carrier source, a phase-locked loop, and an auxiliary feedback pathway, as illustrated at FIG. 2.

Vital sign detection using CW Doppler radar can involve transmitting a microwave signal, which is then phase-modulated by the chest surface displacement, and then receiving and demodulating the reflected signal to obtain vital sign information. In the detection process, residual phase noise and path noise may contaminate the received wave, reducing the quality of the phase information. The residual phase noise, which may be due to the deterioration of phase coherence between the received and local waves, can affect the beat signal, so it can be considered as the phase noise of the reflected signal for convenience of analysis. As the vital sign information can be contained in the phase of the reflected signal, phase noise should be suppressed to extract a low-noise vital sign signal. Considering the reflected signal as a free running VCO that has a high phase noise level, the reflected signal can be phase-locked to a low-noise, highly stable reference signal. Noise within the loop bandwidth can be suppressed, as the phase-locked loop can be a high-pass filter to the free running VCO. Since the vital sign signal is also within the loop bandwidth, the phase-locked loop will suppress the desired vital sign signal as well as the noise if a single carrier is used. To extract the vital sign signal and reduce the noise at the same time, a dual-carrier scheme can be used.

Embodiments of the present disclosure can comprise a non-contact vital sign detection system 200 comprising a dual-carrier source 210 that can reduce the phase noise, as shown in FIG. 2. The non-contact vital sign detection system 200 can comprise microwave signal sources, power amplifiers, frequency converters, antennas, a phase frequency discriminator, a low-pass filter, and a VCO. A microwave signal generator 203 (HP 83622B) and PNA network analyzer 205 (Agilent N5222A) can be phase-locked to a 10-MHz reference signal (215) generated by a 10 MHz reference oscillator and generate 5.60- and 5.68-GHz microwave signals, respectively, and as shown. These two carrier signals can then be power-combined at 213 and directed to the LO port of an I/Q frequency upconverter 240 (Hittite HMC925LC5), with the intermediate frequency (IF) signal provided by an 80-MHz VCO (237). The I/Q frequency upconverter 240 can frequency modulate the two carrier signals with the IF signal. After the frequency of the carrier signals is upconverted by 80 MHz, each carrier signal can be amplified and split into two branches. One branch can be in communication with the TX antenna 247 and provide the frequency-modulated carrier signals 243*a* to the TX antenna 247. The TX antenna 247 can then wirelessly transmit the frequency-modulated carrier signals 243*a* to the propagation pathway over which the carrier signals 243*a* are modulated by the vital sign signal 260, to produce a reflected signal 243*b*. Then, the reflected signals 243*b* can be received by the RX antenna 249. The other branch can provide an auxiliary feedback path 241 to the phase-locked loop to ensure stability is achieved during vital sign detection. The auxiliary feedback path 241 can ensure that the minimum power is achieved to lock the loop. For instance, in an embodiment, the auxiliary feedback path can provide a power level of around 18 dBm, which, in this instance, is the minimum power required to lock the loop when there is no RX received signal.

The reflected signals 243b from the propagation pathway can be power-amplified and received at a frequency down-converter 250 along with the transmission signal from the auxiliary feedback path and the local 5.68-GHz microwave signal, generated by the PNA Network Analyzer 205. The frequency down-converter 250 can mix these signals and frequency downconvert them to an 80-MHz beat signal 235 and low frequency signals, as well as their noise, including residual phase noise and path noise.

The phase-locked loop can then lock the 80-MHz beat signal 235 to the 10-MHz reference signal 215, and the phase-locked loop can control the VCO's (237) phase to stabilize the phase of the 80-MHz beat signal 235. This means the VCO (237) can pre-cancel the residual phase noise and path noise in the transmitted carriers so that the 80-MHz beat signal 235 and its corresponding received 5.76-GHz carrier have a low phase noise but contain approximately no vital sign information, which can be considered path noise. This system can then provide a clean transmission path for the frequency-modulated, 5.60-GHz carrier (upconverted to 5.68-GHZ). The demodulation of the 5.68-GHz upconverted signal with the 5.68-GHz local signal can provide a low-noise vital sign signal that can be acquired and analyzed to extract relevant information about the detected vibratory signal.

Time Domain Mathematical Analysis

Figure 3A:
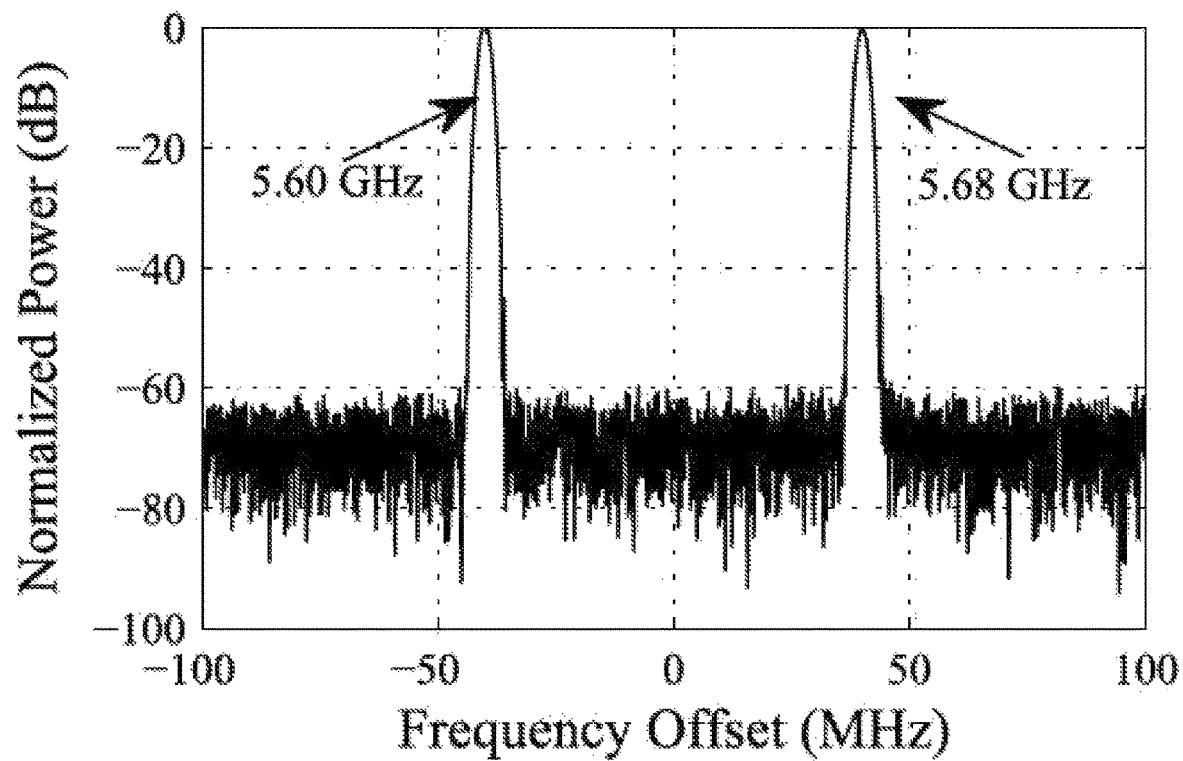
FIGS. 3a and 3b is a graphical representation of the normalized power measured for phase-locked microwave signals as a function of the frequency offset, in accordance with one embodiment of the present disclosure.
Figure 3B:
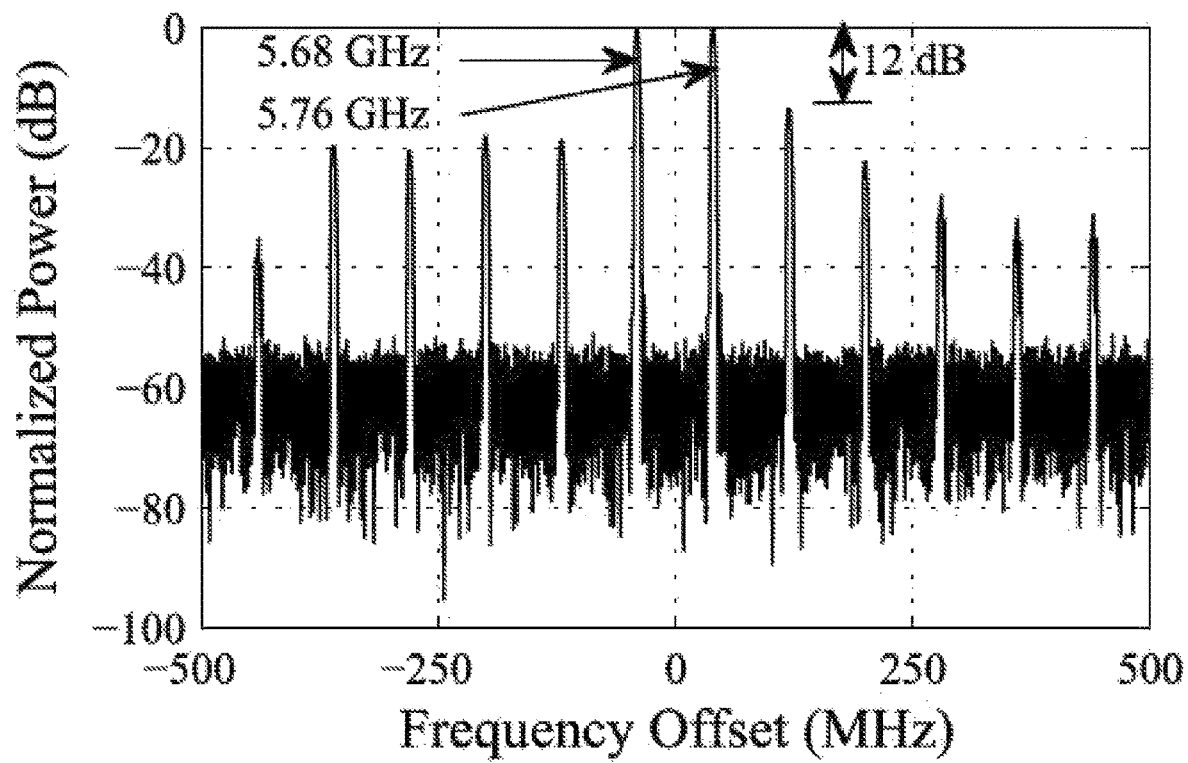

The microwave signals from the microwave signal generator and PNA network analyzer can be expressed as:

$$v_1(t) = \sin(2\pi f_a t + \varphi_a) + \sin(2\pi f_b t + \varphi_b) \quad (1)$$

where $f_a$ and $f_b$ are 5.68- and 5.60-GHz, respectively, while $\varphi_a$ and $\varphi_b$ are the corresponding phases of the two signals, respectively. The two signals can be amplified and adjusted to have the about the same power at the LO port of the frequency upconverter. FIG. 3a is a graphical representation of the normalized power associated with the 5.68- and 5.60-GHz signals as a function of the frequency offset.

Then the microwave signals can be mixed with the 80-MHz VCO signal to output the frequency upconverted signals at the RF port of the frequency upconverter. The frequency upconverted signals can be expressed as:

$$v_1(t) = \sin[2\pi(f_a + f_v)t + (\varphi_a + \varphi_v)] + \sin[2\pi(f_b + f_v)t + (\varphi_b + \varphi_v)] \quad (2)$$

where $f_v$ is 80-MHz and $\varphi_v$ represents the phase of the VCO. After being amplified, the upconverted signals can be transmitted through the TX antenna. The spectrum of the frequency upconverted signals is illustrated in the graphical representation at FIG. 3b. Due to the properties of the VCO and the frequency upconverter, there may be unwanted sidebands around the desired 5.76- and 5.68-GHz. These sidebands can spread in a span of about 2.5-GHz, with a space of 80-MHz. By adjusting the power level and delay/phase at the LO and IF ports of the frequency upconverter, the ratio between the carrier and the unwanted sidebands can reach 12-dB. When mixed with a 5.68-GHz local signal in the frequency downconverter (Hittite HMC951LP4E), both 5.76- and 5.60-GHz signals can produce the 80-MHz beat signal, which can be fed back to lock the loop. Thus the 5.60-GHz sideband component can influence the system performance, but the 20-dB ratio to 5.76-GHz signal may significantly reduce such an effect. The higher order sidebands have little influence on the performance of the system, as the bandpass filter will filter out their corresponding beat signals. Thus, the sidebands can be neglected for the purpose of the following analysis, with focus only on the 5.68- and 5.76-GHz signals.

After being transmitted from the TX antenna, the microwave signals can be phase-modulated by the vital sign signal, including the heartbeat and respiration. Assuming the displacement of the human chest is x(t), it will contribute to a delay of $\tau_x = 2 x(t)/c$ or a phase of $\varphi = 2\pi f \tau_x = 4\pi x(t)/\lambda$, where $\lambda$ is the speed of electromagnetic wave and $\lambda$ is the wavelength. Thus, the vital sign signal can be detected through analyzing the phase of received microwave signals.

The microwave signals received by the RX antenna contain a vital sign signal as well as noise associated with that signal:

$$v_3(t) = \cos[2\pi(f_a + f_v)(t+\tau) + (\varphi_a + \varphi_v + \varphi_n)] + \cos[2\pi(f_b + f_v)(t+\tau) + (\varphi_b + \varphi_v + \varphi_n)] \quad (3)$$

where $\varphi_n = \varphi_{pa} + \varphi_{rd}$, $\varphi_{pa}$ and $\varphi_{rd}$ represent the path noise and residual phase noise, respectively, and $\tau = \tau_x + \tau_0$ with $\tau_0 = 2d_0/c$ is ascribed to the average distance $d_0$ between the chest and the antenna. The reflected signals may have a low power level, so a low-noise power amplifier (Hittite HMC902LP3) can be incorporated to adjust the power level of the reflected signals. After amplification, the received signals can be combined with the auxiliary path signals. The auxiliary path signals may help to improve the locking performance of the system, especially when the amplified received signals are a little lower than 18 dBm, which is required to produce a 10-dBm minimum feedback signal for the phase-frequency detector.

The effect of the auxiliary path on the extraction of vital sign signals can be analyzed as follows. To analyze the effect of auxiliary path on the noise performance of the vital sign signal, the amplitude ratio between the auxiliary path and the received signal can be assumed to be a. Thus, the IF port of frequency downconverter is:

$$v_4 = \sin(\Theta_a) + \sin(\Theta_b) + \alpha \sin(v_a) + \alpha \sin(v_b) = \sin(\Theta_a) + a \sin(v_a) + \alpha \sin(\Theta_b) + a \sin(v_b) \quad (4)$$

where $$\Theta_a = \omega_v t + (\omega_a + \omega_v)\tau + \varphi_v + \varphi_n, \quad (4a)$$

$$\Theta_b = (\omega_b - \omega_a + \omega_v)t + (\omega_b + \omega_v)\tau + (\varphi_b - \varphi_a + \varphi_v + \varphi_n), \quad (4b)$$

$$v_a = \omega_v t + (\omega_a + \omega_v)\hat{\tau} + \varphi_v + \hat{\varphi}_n \quad (4c)$$

$$v_b = (\omega_b - \omega_a + \omega_v)t + (\omega_b + \omega_v)\hat{\tau} + (\varphi_b - \varphi_a + \varphi_v + \hat{\varphi}_n) \quad (4d)$$

Here, $v_a$ and $v_b$ are the phases of carriers a and h in the auxiliary path. $\hat{\tau}$ and $\hat{\varphi}_n$ represent the delay and noise introduced by the auxiliary path.

Through the mathematical transform, $v_6(t)$ can be rewritten as:

$$v_6 = (1+\alpha)\sin(x_a)\cos(y_a) + (1-\alpha)\cos x_a \sin y_a \quad (5)$$

where $x_a = (\theta_a + v_a)/2$ and $y_a = (\theta_a - v_a)/2$.

In the short distance ($\alpha \ll 1$), $1+\alpha \approx 1-a$. Thus $v_6(t)$ will be $v_6 = \sin(x_a + y_a) = \sin(\theta_a)$, which implies that the auxiliary path does not influence the vital sign detection. If the ratio $\alpha$ is increasing to 1, $v_6 = 2 \sin(x_a) \cos(y_a)$. The cosine term is the slow amplitude fluctuation, and the amplitude noise of the controlled oscillation system can be ignored in the phase-locked loop. $v_6$ is locked to the reference signal $v_5$, so $\phi_6 = x_a = 8(\omega_{ref} + \varphi_{ref})$, thus $$v_7 = 2\sin\left[8\phi_{ref} + \frac{w_b - w_a}{2}(\tau + \hat{\tau}) + \phi_b - \phi_a\right] \quad (6)$$

where $\hat{\tau}$ is the delay introduced by the auxiliary path, and it is much smaller than $\tau$. When the ratio is around 1, the effect of the auxiliary path can be neglected. So the vital sign signal is not degraded in the short distance.

As the detection distance extends, the effect of the auxiliary path on the vital sign will become apparent. In the long distance ($\alpha \gg 1$), $v_6 = \alpha \sin(x-y_a) = \sin(\vartheta_a)$, the loop is totally locked through the auxiliary path. Without the auxiliary feedback path, the system may have difficulty with detecting the vital sign signal.

If the auxiliary path is at a lower power, it typically can perform better. However, it should demonstrate enough power to provide a −10 dBm of $v_6$, required by the datasheet of phase-frequency detector used in the described systems. In some embodiments, to achieve a −10 dBm of $v_6$, the auxiliary feedback path should be about −18 dBm, which is the minimum power required to lock the loop when there is no RX received signal. The auxiliary path can then provide a stable detection when the amplified reflected signal is even lower than −18 dBm. In embodiments where the amplified received signal is over −18 dBm, the auxiliary path is optional. Then the combined microwave signals can be mixed with a 5.68-GHz local signal split from the PNA network analyzer, producing beat signals at the frequency downconverter IF port:

$$v_4(t) = \sin[2\pi(f_v)t + 2\pi(f_a + f_v)\tau + \phi_v + \varphi_n] + \quad (7)$$
$$\sin[2\pi(f_b - f_a + f_v)t + 2\pi(f_b + f_v)\tau] + (\phi_b - \phi_a + \phi_v + \varphi_n)]$$

where $f_b - f_a + f_v$ equals 0. The beat signals can be split into two branches, one of which is directed to a low-pass filter having cutoff frequency of 20-kHz to extract the vital sign signal. The other branch can pass through a 58-82-MHz bandpass filter, and the harmonics of 80-MHz beat signal can be filtered out. Then the 80-MHz beat signal corresponding to the first term of $v_4(t)$ can be fed back to the phase-frequency detector, where it can be divided into 10-MHz and discriminated with the 10-MHz reference:

$$v_5(t) = \sin(2\pi f_{ref} t + \varphi ref) \quad (8)$$

where $f_{ref}$ and $\varphi_{ref}$ are the frequency and phase of the reference oscillator, respectively. The phase frequency detector can discriminate the phase difference of the beat signal and the reference signal and output an error signal. This signal can be filtered by the low-pass filter and then drive the VCO to produce an 80-MHz IF signal, with a phase that can be pre-adjusted to cancel the noise and achieve a low-noise 80-MHz beat signal. When the loop is locked, the phase relationship between $v_5(t)$ and the first term of $v_4(t)$ may be:

$$[2\pi(f_a+f_v)\tau+\varphi_n]+\varphi_v=8\varphi_{ref} \quad (9)$$

With (9), the beat signal $v_4(t)$ can be written as:

$$\tilde{v}_4(t)=\sin(2\pi f_v t+8\varphi_{ref})+\sin\left[2\pi(f_b-f_a+f_v)t+2\pi(f_b-f_a)\tau+(\varphi_b-\varphi_a+8\varphi_{ref})\right] \quad (10)$$

By phase-locking the 80-MHz beat signal to the 10-MHz reference signal provided by the low-noise reference oscillator, the phase-locked loop can control the VCO to pre-adjust its phase. Thus the phases of the transmitted carriers can be adjusted for canceling the residual phase noise and path noise. As a result, the phase noises of both the beat terms shown in $\tilde{v}_4(t)$ can be suppressed to the level of the reference.

By passing the beat signals through the low-pass filter, the 80-MHz beat signal can be filtered out, and the time domain vital sign signal can be obtained in the oscilloscope. Combined with $f_b-f_a+f_v=0$ and $\tau=\tau_x+\tau_0$, the second term of $\tilde{v}_4(t)$ represents the vital sign signal.

$$v_7(t) = \sin\left\{\left[2\pi(f_b-f_a)\left[\frac{2d_0}{c}+\frac{2x(t)}{c}\right]+(\varphi_b-\varphi_a+8\varphi_{ref})\right\} \quad (11)$$

Here, $d_0$ is constant and $\varphi_{ref}$ is low noise in the system. As both the 5.60- and 5.68-GHz signals are phase-locked to the 10-MHz reference, $\varphi_b-\varphi_a$ has a noise level similar to that of $8\varphi_{ref}$. Therefore, the noise in $v_7(t)$ is suppressed when the loop is locked, resulting in low noise in the vital sign signal.

Frequency Domain Mathematical Analysis

Figure 4:
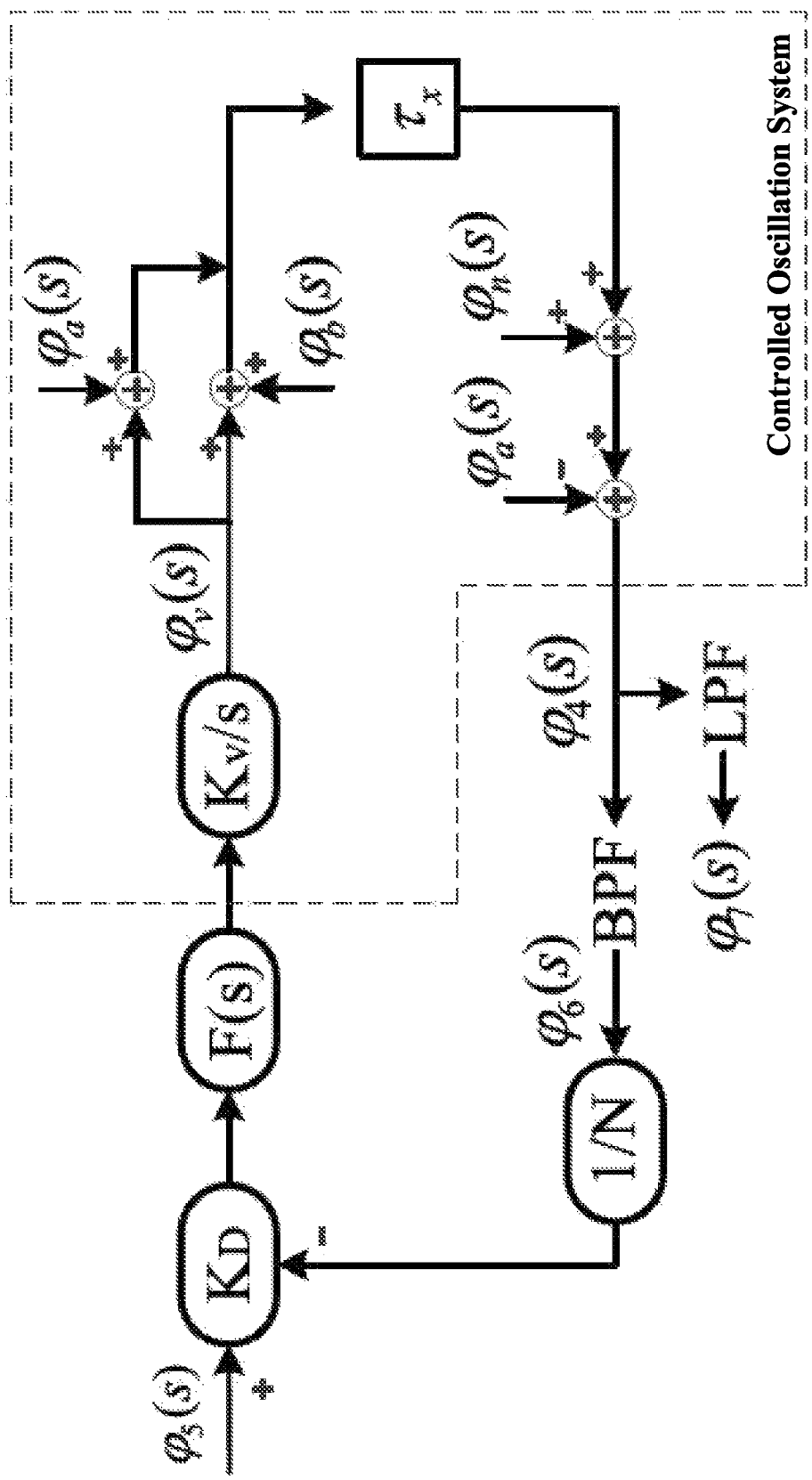
FIG. 4 is a linear frequency domain model relating to an embodiment of a non-contact signal detection system, in accordance with one embodiment of the present disclosure.

For purposes of understanding the noise suppression mechanism, FIG. 2 can be simplified to a linear frequency domain model, as shown in FIG. 4. The noise and vital sign signals ($\tau_x$) are contained in the frequency downconverted signals $\varphi_4(s)$. After the band (BPF) and low-pass (LPF) filtering, the beat signal (noise information) $\varphi_6(s)$ and vital sign signal $\varphi_7(s)$ can be obtained, where $\varphi_6(s)$ and $\varphi_7(s)$ correspond to carriers a and b, respectively:

$$\varphi_6(s)=[\varphi_v(s)+\varphi_a(s)]e^{-s\tau x}-\varphi_a(s)+\varphi_n(s) \quad (12)$$

$$\varphi_7(s)=[\varphi_6(s)]+[\varphi_b(s)-\varphi_a(s)]e^{-s\tau x} \quad (13)$$

where $\varphi_a(s)=A\varphi_5(s)$, $\varphi_b(s)=B\varphi_5(s)$), and A and B are the frequency ratios between their carriers and reference, respectively, as carrier a and b can be locked to the reference signal $\phi_5(s)$ at a phase-frequency detector ($K_D$). As illustrated at FIG. 4, the feedback signal can also be locked to $\varphi_5(s)$, and $\varphi_6(s)=N\varphi_5(s)$. Thus the transfer function between the vital sign signal and reference, $H(s)=\phi_7(s)/\phi_5(s)$, can be written as $$H(s)=N+(B-A)e^{-s\tau x} \quad (14)$$

Therefore, the noise performance of the vital sign signal can be determined by that of the reference signal, and the path and residual phase noise can be suppressed using the phase-frequency detector, low-pass filter, and the VCO ($K_d$, F(s), and $K_v/S$ respectively). The vital sign can be extracted as shown in (14). The transfer function of the noise can be very complex, but it can be seen in FIG. 4 that $\varphi_n(s)$ is the noise of the controlled oscillation system. In the phase-locked loop, the noise can be high frequency passed and can be suppressed in the low-frequency vital sign signal. Thus the noise and vital sign signal can be suppressed and extracted through carriers a and h, respectively.

Figure 5:
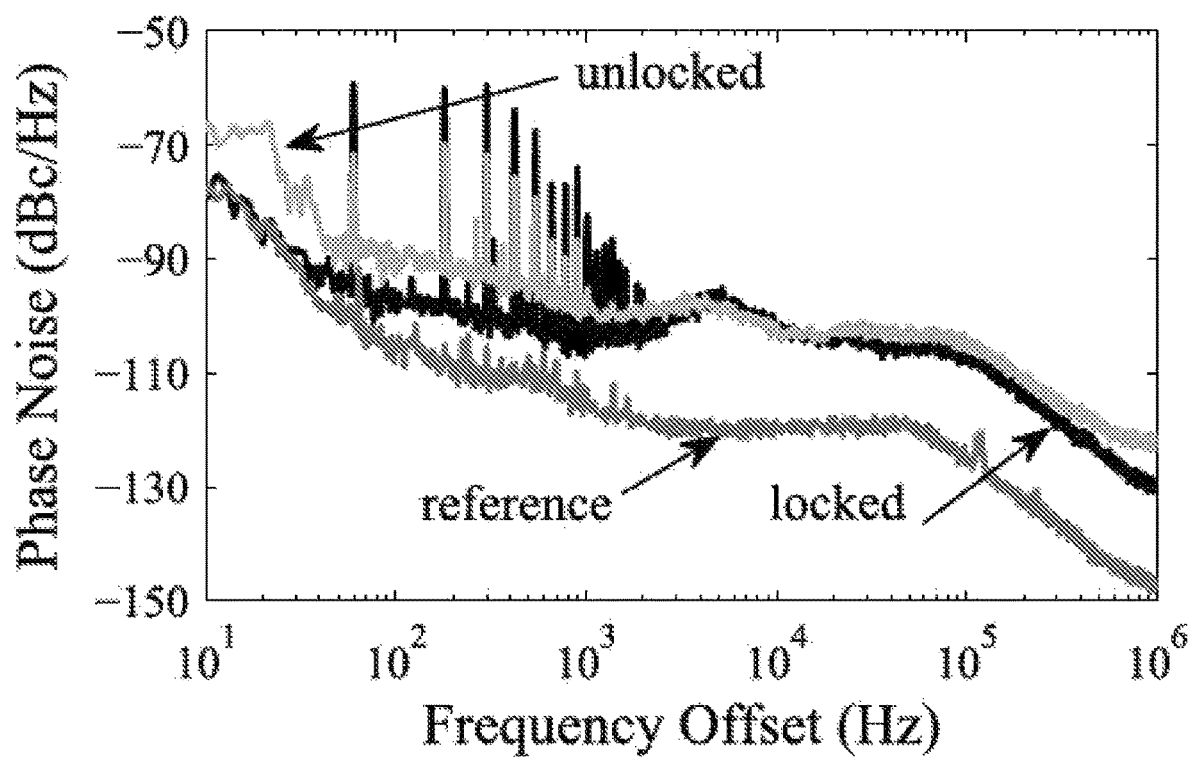
FIG. 5 is a graphical representation of the measured phase noise spectrum of the beat signal and the reference signal when unlocked and locked, in accordance with one embodiment of the present disclosure.

Due to the very low frequency of the vital sign signal ($\tau_x$) it may prove hard to exhibit the performance of phase noise suppression through the spectrum of (14). The 80-MHz feedback beat signal $\varphi_6(s)$, which is the first term of (13), can be used to demonstrate the noise suppression performance as it has the same suppression ratio as the vital sign signal. Its phase noise spectrum measured with a spectrum analyzer (Agilent E4440A) is shown in FIG. 5. As a comparison, the phase noise spectra of the reference and the beat signal of an unlocked system are also provided. The unlocked system can be a modified system in FIG. 2 by connecting the RF port of phase-frequency detector ($K_D$) to VCO ($K_v/S$) output instead of the down-converted signal and disconnecting the auxiliary feedback.

FIG. 5 shows that the 80-MHz beat signal of the locked system, which can be a controlled oscillation system to the loop, has a suppressed phase noise within the 10-kHz loop bandwidth and exhibits a noise level that is about 12-dB lower than the unlocked case at the 10-Hz frequency offset. Up to 50-Hz frequency offset, it can be stabilized to the reference signal and has almost the same noise level. At a frequency offset of more than 10 kHz, which is the loop bandwidth, the noises are not suppressed due to phase-locked loop's high-pass characteristics for the controlled oscillation system's signal. This demonstrates that the phase-locked loop can successfully suppresses the residual phase noise and path noise, which facilitates detection of a clean vital sign signal.

Results

Figure 6:
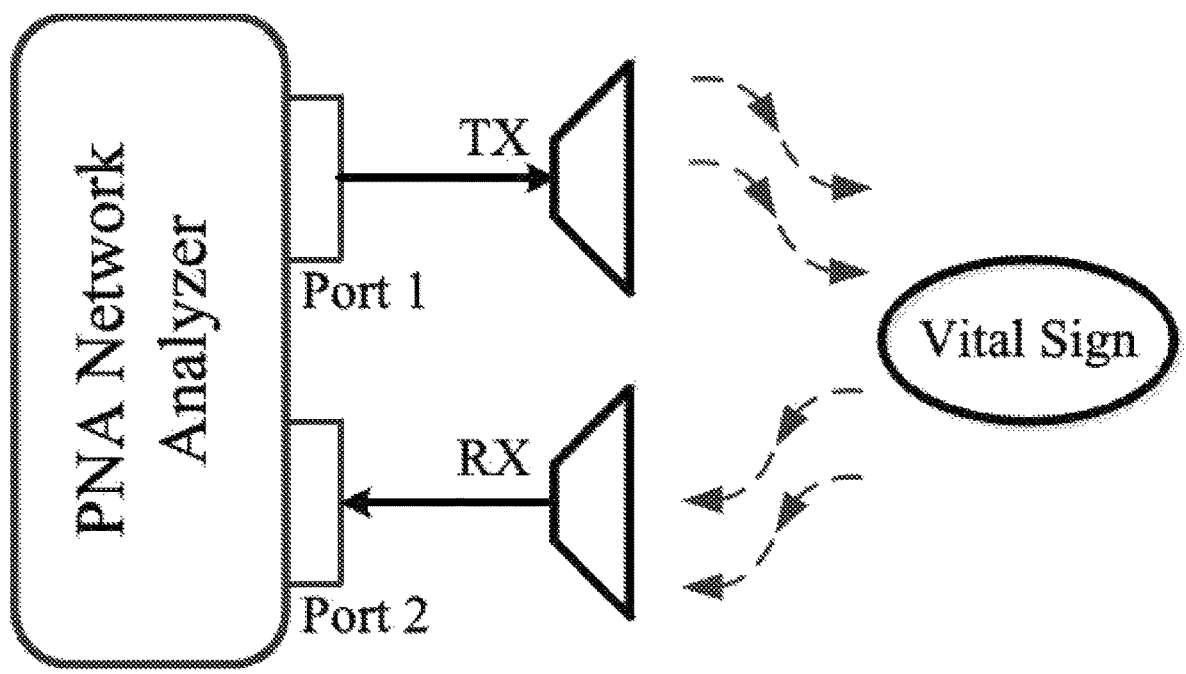
FIG. 6 is a schematic of a prior art, direct vital sign detection having a transmitter antenna and a receiver antenna in communication with a PNA Network Analyzer.

To verify that the systems described in accordance with FIGS. 2-5 introduce no extra noise, the measurement result of the unlocked system, which is a modified design in FIG. 2 as mentioned before, was compared with that collected by a direct vital sign detection system shown in FIG. 6. In the direct measurement scheme, the PIMA network analyzer transmits a microwave signal, receives and demodulates the reflected signal, and then displays a time domain vital sign signal. The transmitting power in port 1 of the network analyzer is approximately 6 dBm, and the antenna is about 50 cm away from the human subject. A time domain signal of 25s was recorded and analyzed in the frequency domain, represented by black lines in FIG. 7a. With the same transmit power and detection distance, the vital sign detected with the unlocked system is exhibited by gray lines in FIG. 7a.

Figure 7A:
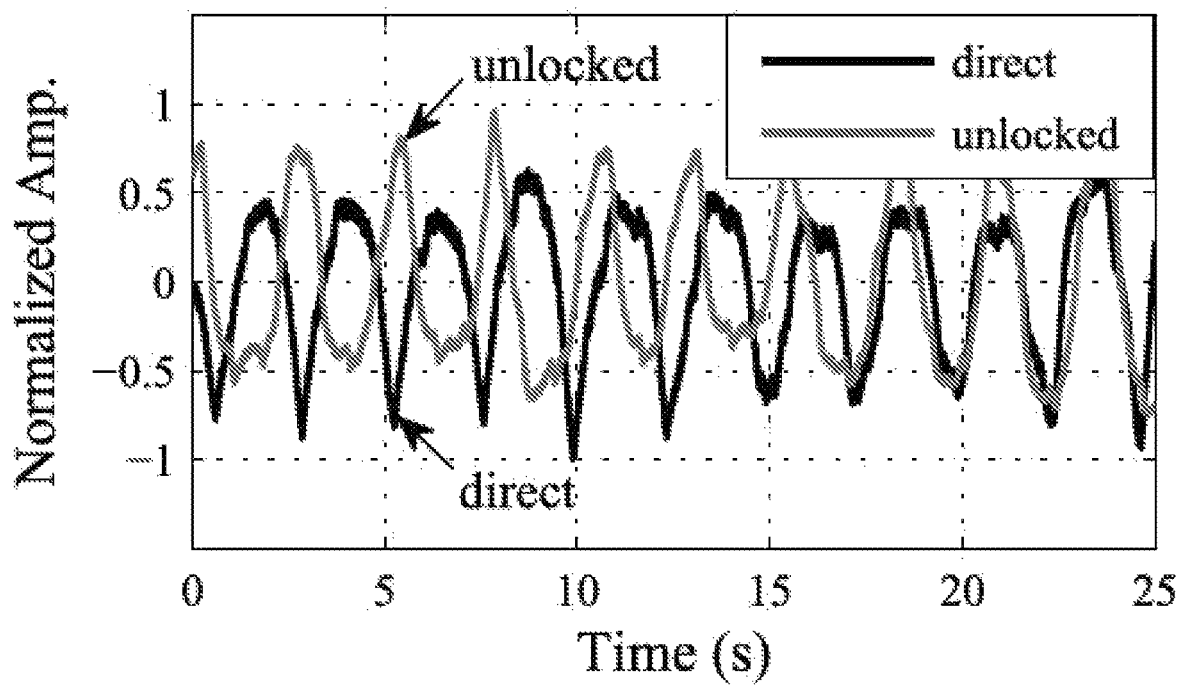
FIGS. 7a and 7b are graphical representations comparing detection of vital sign signals with a direct signal (black line) and an unlocked system (gray line).
Figure 7B:
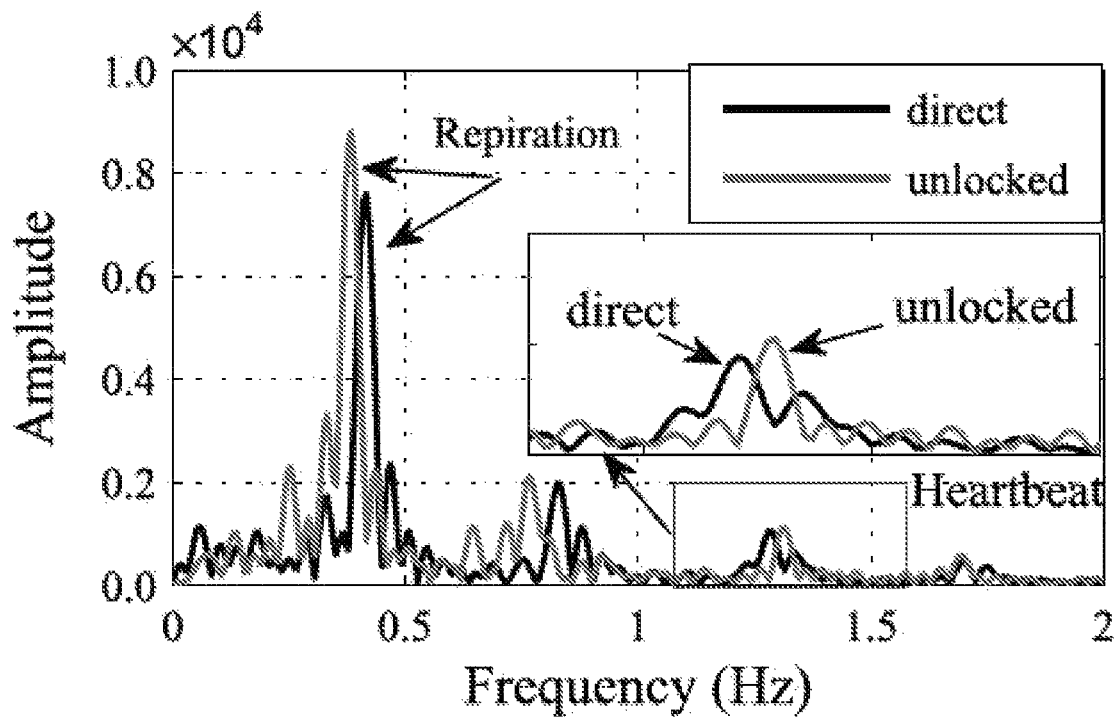

In the time domain, respiration may be obvious, but the heartbeat, which is superimposed on the respiration signal, may, in some instances be hard to recognize. Using fast Fourier transform, the vital sign signal can be represented in the frequency domain as shown in FIG. 7b. The respiration frequency through direct measurement scheme can be 0.41 Hz, and the unlocked case can have a respiration frequency of 0.38 Hz. The frequency difference may be due to the status of the subject, as the experiments are not conducted at the same time. The heartbeat, which may not be as obvious or strong as the respiration signal, has a frequency of around 1.3 Hz. As shown in the inset of FIG. 7b, the amplitude and frequency of heartbeat in the two schemes are almost the same. Given that the results of the vital sign measurements from the unlocked system and the direct detection are similar, the additional system components in the described systems do not introduce obvious extra noise.

Figure 8A:
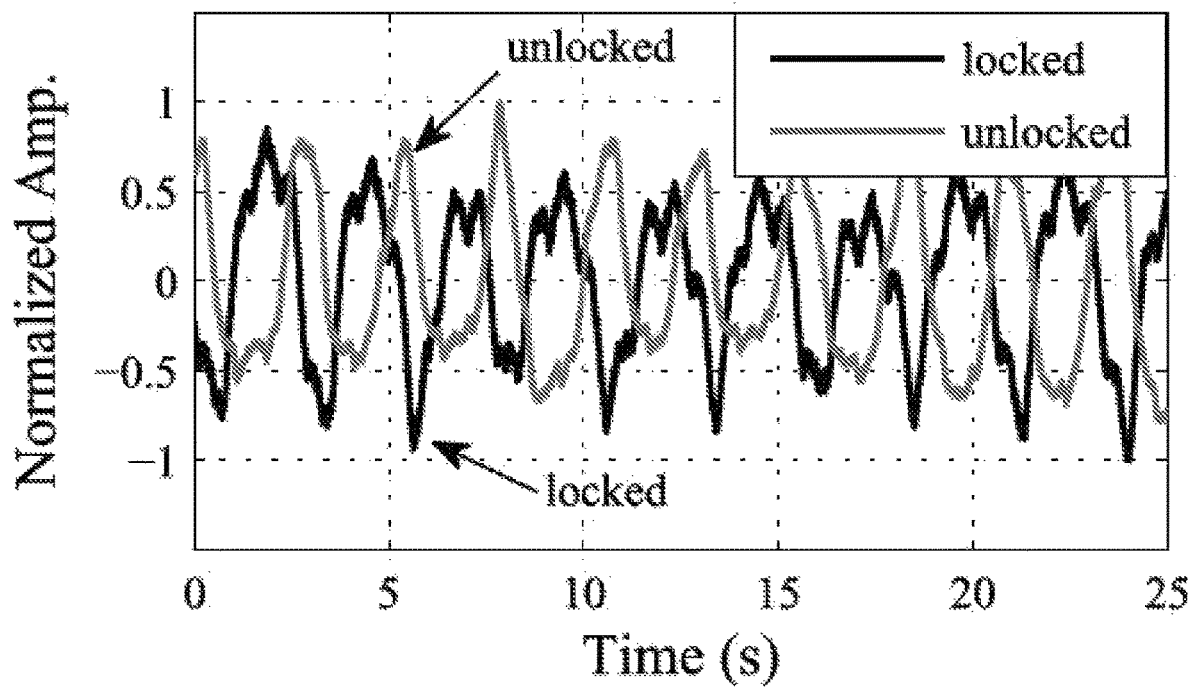
FIGS. 8a and 8b are graphical representations comparing detection of vital sign signals with a locked system (black line) and an unlocked system (gray line), in accordance with one embodiment of the present disclosure.
Figure 8B:
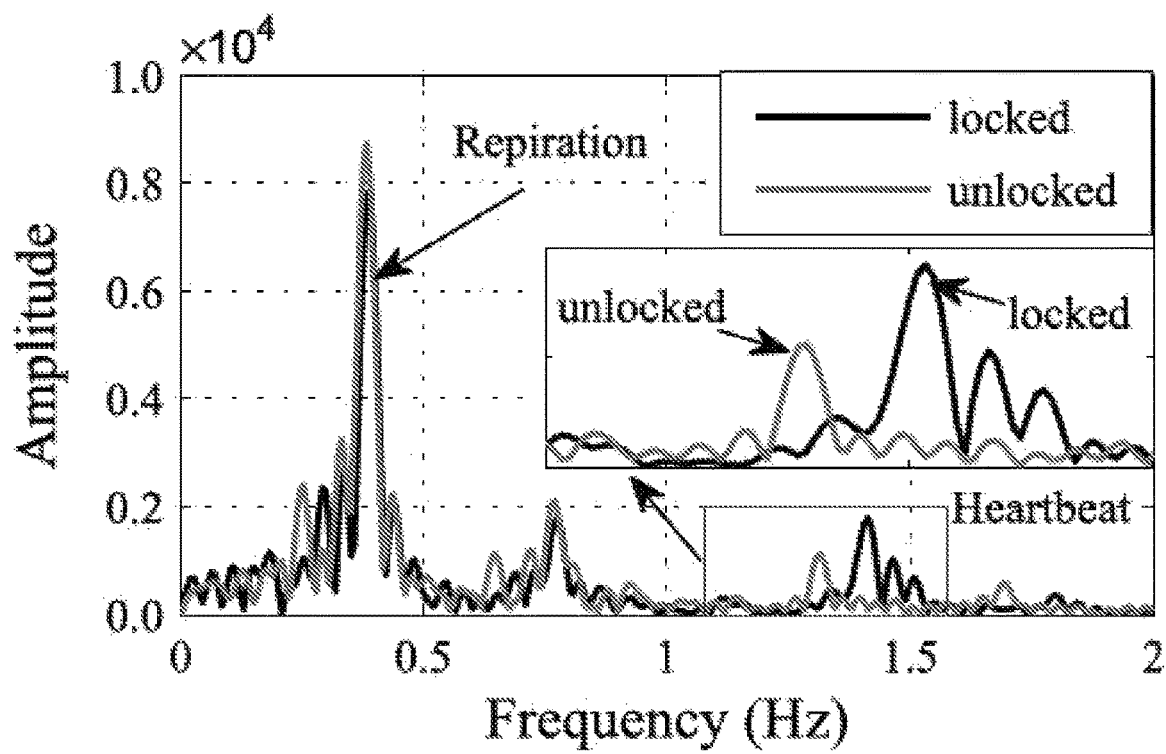
Figure 9A:
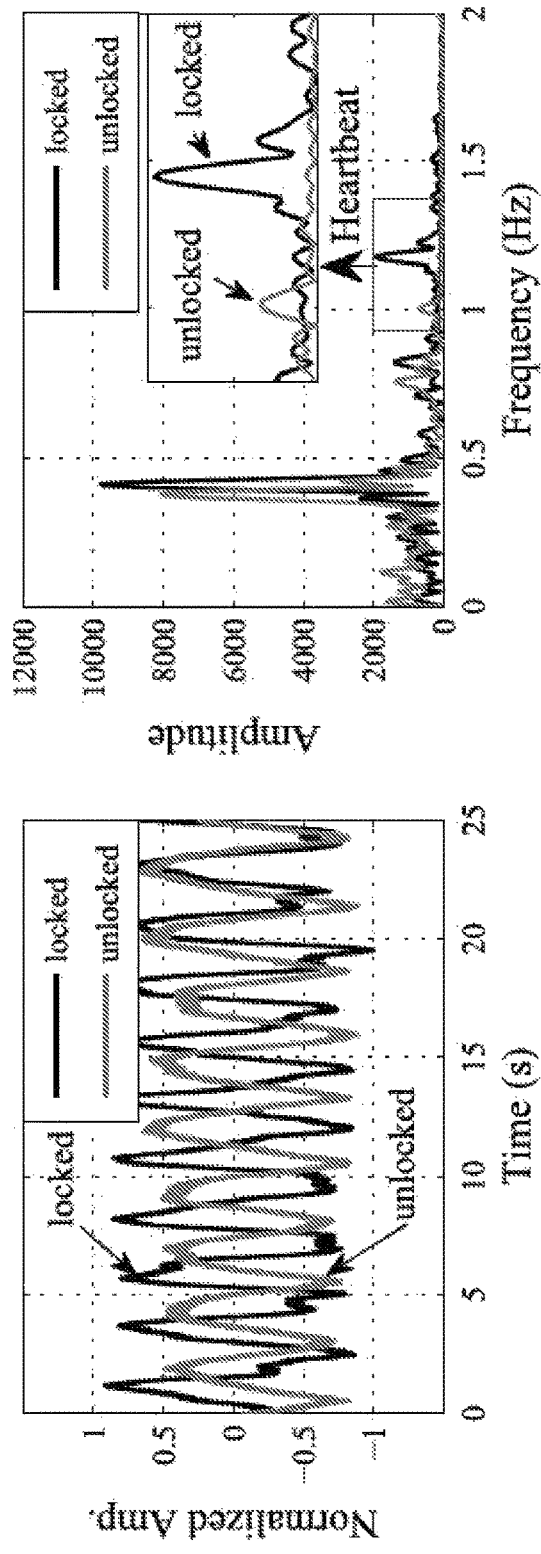
FIGS. 9a-9e are graphical representations comparing detection of vital sign signals with a locked system and an unlocked system at various distances away from a subject, including 100 cm (FIG. 9a), 150 cm (FIG. 9b), 200 cm (FIG. 9c), 250 cm (FIG. 9d), and 300 cm (FIG. 9e), in accordance with one embodiment of the present disclosure.
Figure 9B:
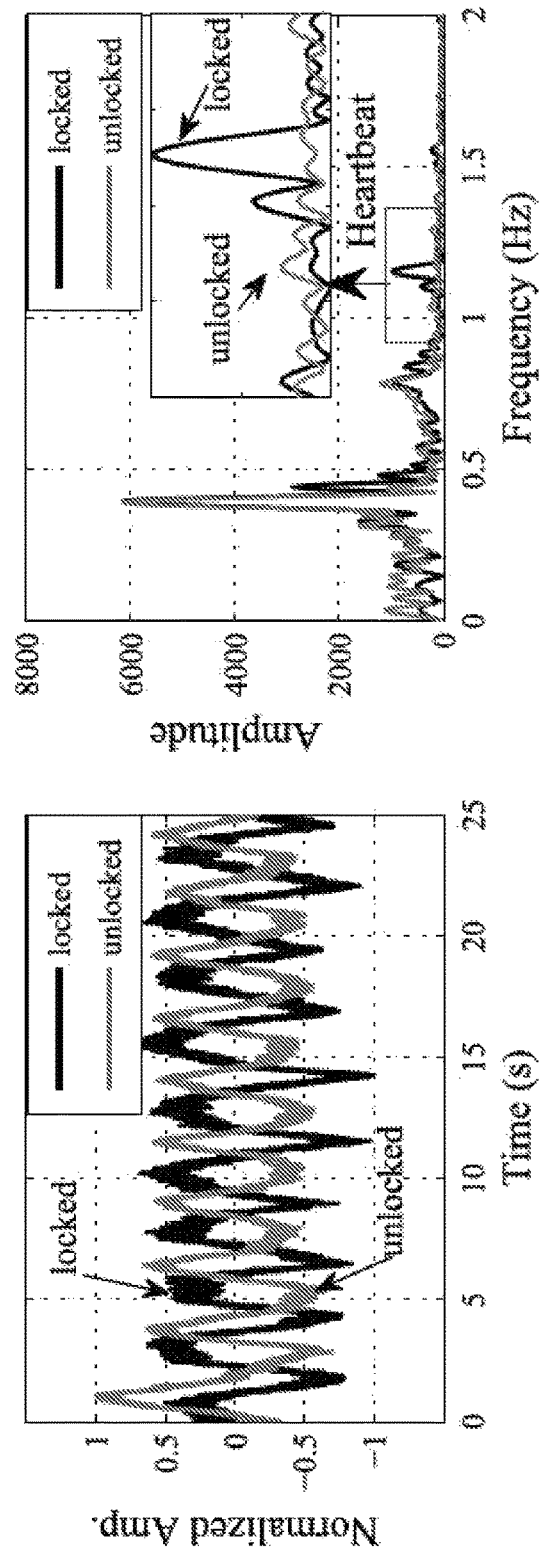
Figure 9C:
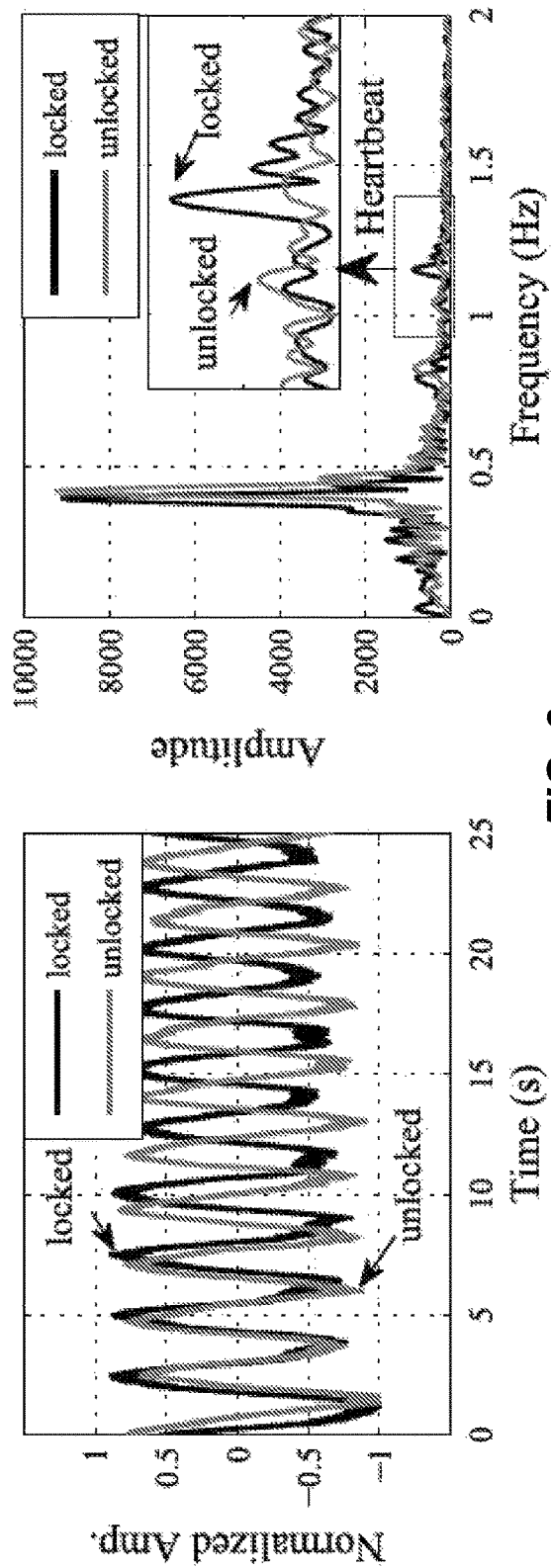
Figure 9D:
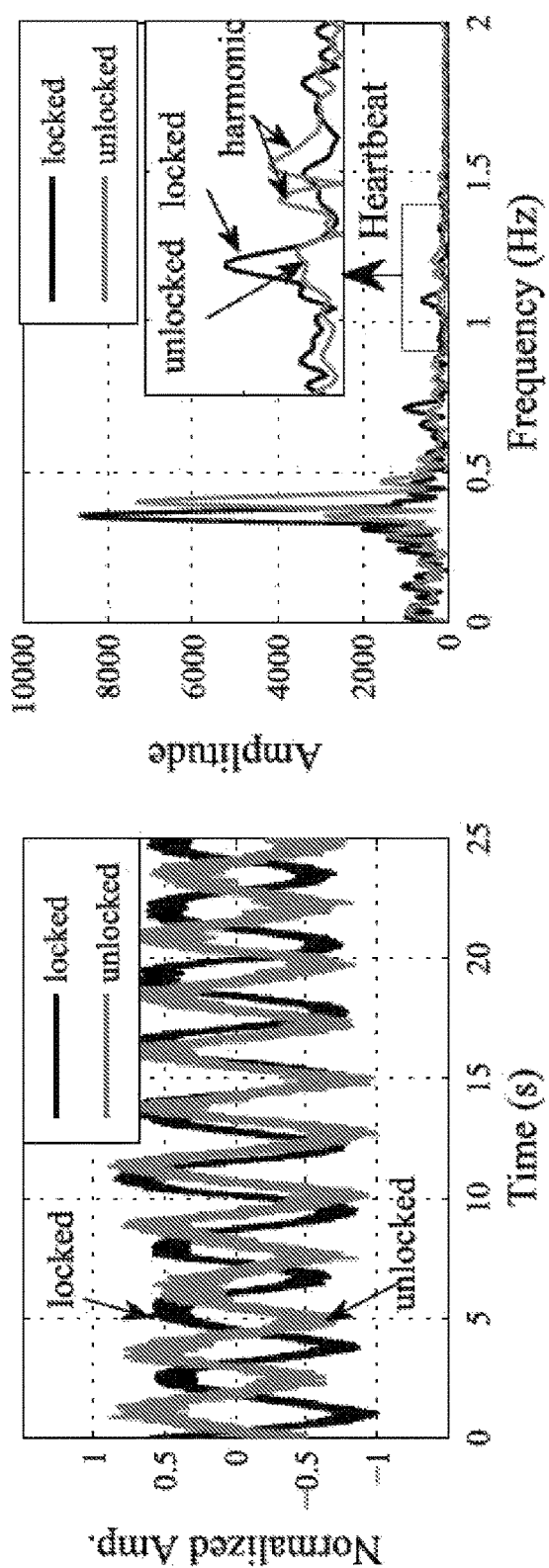
Figure 9E:
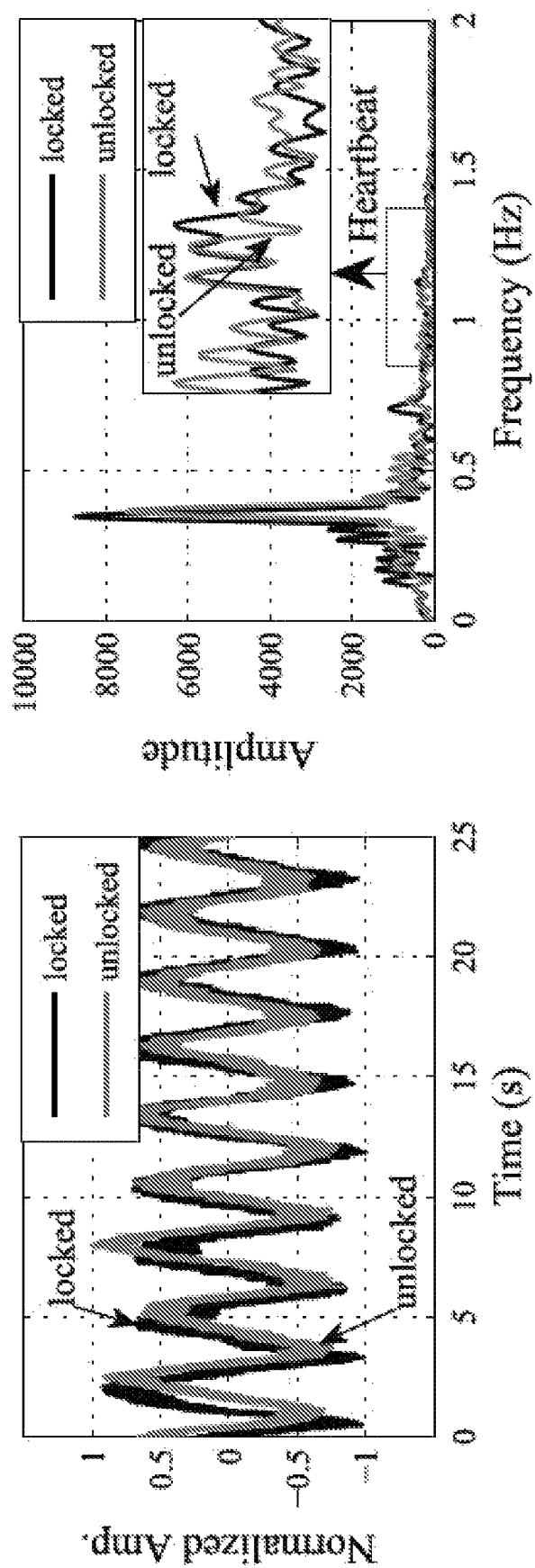

The unlocked system was compared with the phase-locked loop design shown in FIG. 2. With the same transmit power and detection distance as in FIGS. 7a and 7b, the vital sign measurement results from both the systems are illustrated at FIGS. 8a and 8b. With the exception that the vital sign signals have slightly different frequencies, the respiration rate from the locked system was quite similar to that of the unlocked case and their amplitudes are similar, which might be due to the condition of the subject. When the loop is locked, uncorrelated phase noise is suppressed. Thus, a clearer heartbeat was obtained, meaning that there was less possibility of inaccuracy in detection.

To further explore the detection performance of the locked system, the measurement distance was altered to 100, 150, 200, 250, and 300 cm without changing the transmit power. As shown in FIGS. 9a-9e, the results of the locked system are represented by black lines, while those of the unlocked system by gray lines. The time domain signal exhibits the periodical fluctuation, which is the respiration with heartbeat superimposed on it. The respirations of both the locked and unlocked systems were around 0.4 Hz and even overlapping in FIG. 9h. For the heartbeat, the locked system has a clear frequency component at about 1.2 Hz, which slightly changes at different detecting distances. As the measurement of the unlocked system was conducted at a different time, the heartbeat frequency detected was around 1.0 Hz.

FIGS. 9a-9e shows that the heartbeat can be detected by the unlocked system at a distance of 100 cm, but it was hard to recognize when the distance exceeds 150 cm. However, the locked system can still detect the heartbeat at 250 cm. At 300 cm, a quite rare wave is reflected back to the loop; therefore, the heartbeat was severely noise-influenced and hard to detect. As respiration has a much larger displacement than heartbeat, both the systems can still detect it at 300 cm.

Figure 10A:
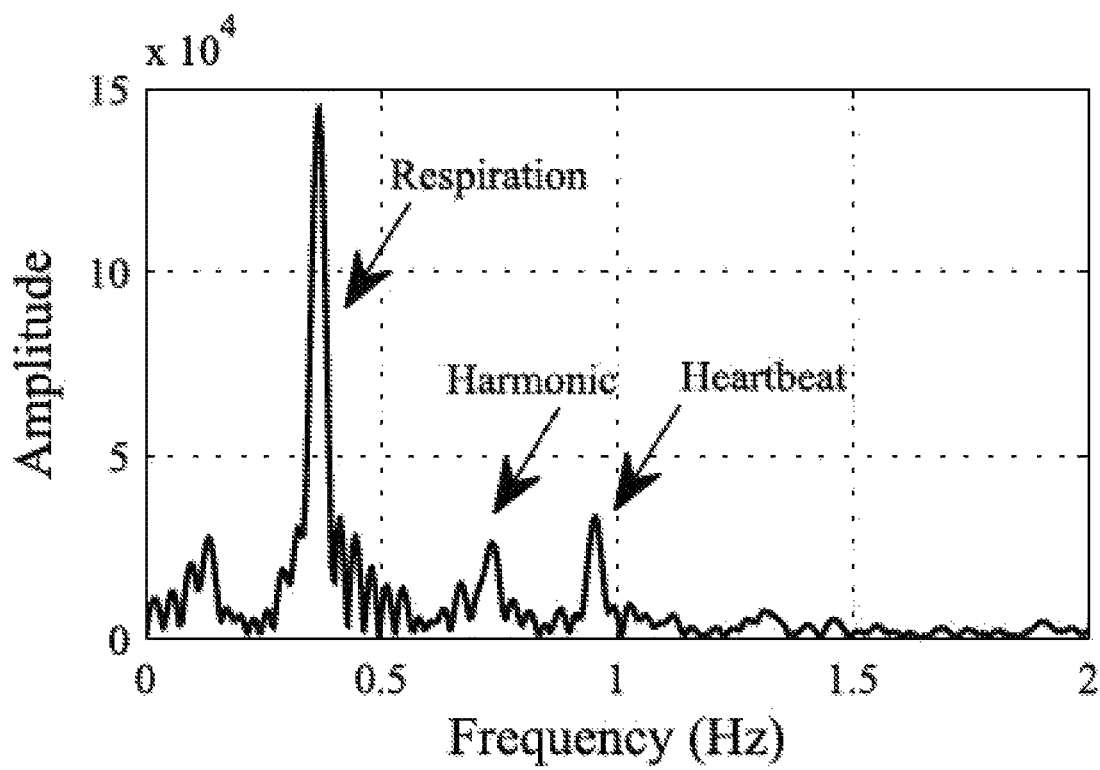
FIGS. 10a-10d illustrate detection of vital sign signals at four orientations of the subject, including facing front (FIG. 10a), facing back (FIG. 10b), facing left (FIG. 10c), and facing right (FIG. 10d), in accordance with embodiment of the present disclosure.
Figure 10B:
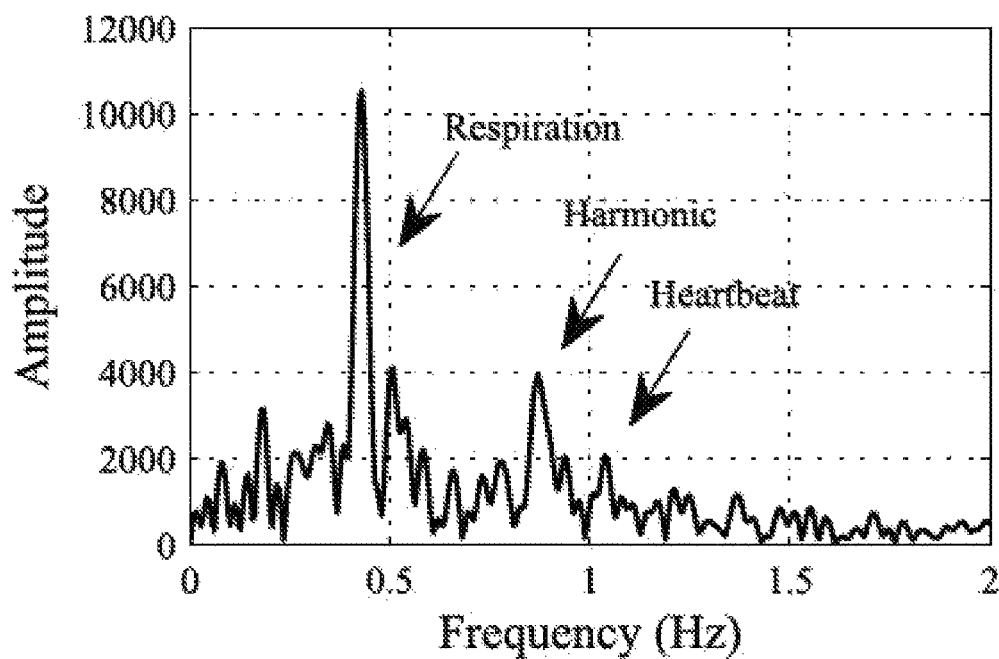
Figure 10C:
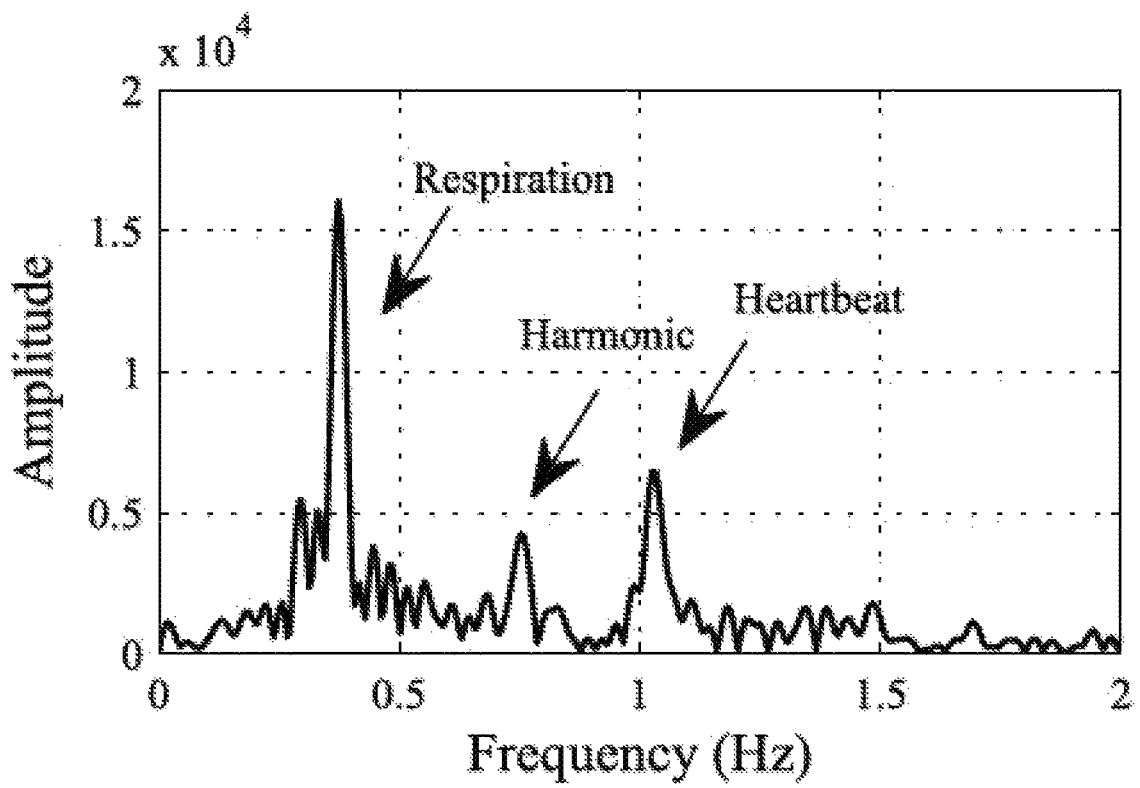
Figure 10D:
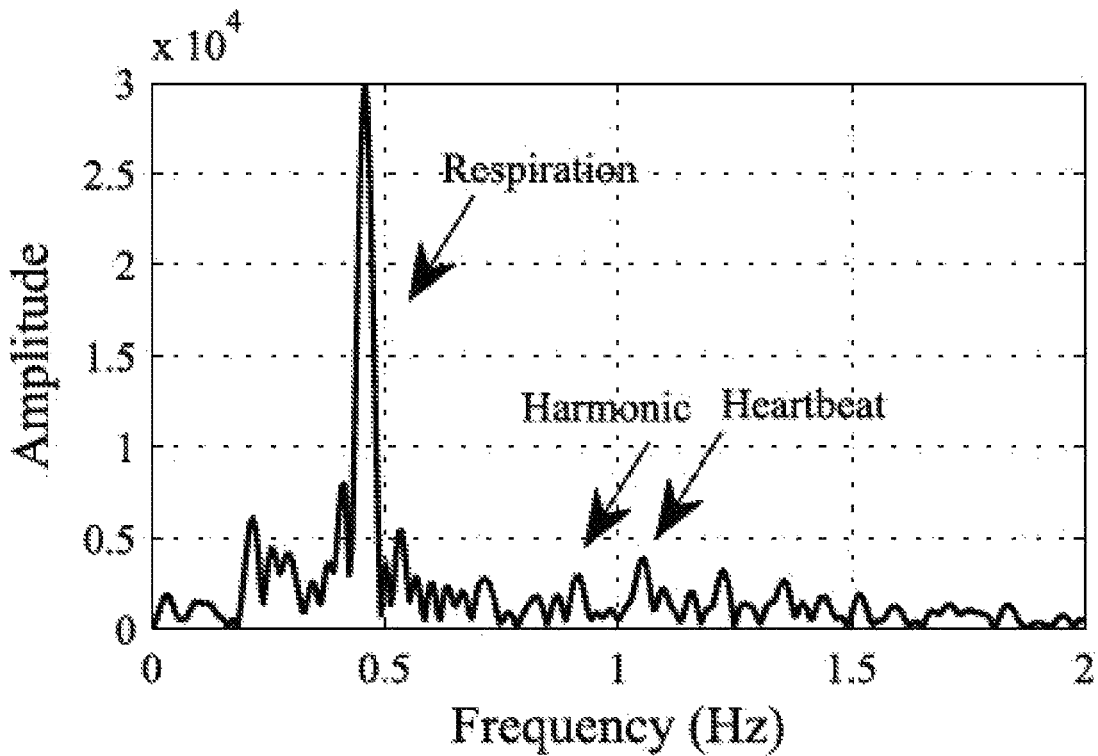

Vital sign detection in four physical orientations was also conducted with the same experimental setup as that in FIGS. 8a and 8h. During the detection, the subject changes the orientation to let the antenna face the front, hack, left, and right sides of the subject. The measurement results for the four orientations are shown in FIG. 10-10d. Respiration can be easily detected in all the four orientations. For the heartbeat signal, it can be detected obviously when facing front and left (FIGS. 10a and 10c). When the antenna faces the back and right sides of the subject, the heartbeat signal is very weak (FIGS. 10b and 10d) due to the less effective reflective area. The back side signal as shown in FIG. 10b has the worst noise level.

Discussion

In accordance with various implementations as described above, a dual-carrier vital sign detection system with a noise suppression scheme based on phase-locked loop was demonstrated to automatically reduce the residual phase noise and path noise. Through the phase discrimination between one carrier's beat signal and the low-noise reference signal in the phase-frequency detector, noise can be extracted and then suppressed in the phase-locked loop, providing a clean transmission path for the other carrier. Therefore, the vital sign signal contained in the phase of the second carrier can be obtained with low noise. Experiments with locked and unlocked system have been carried out to compare the noise and detection performance. The results show that systems in accordance with embodiments of the present disclosure, can effectively suppress the residual phase noise and path noise, improving the SNR by about 12 dB at 10-Hz frequency offset, and significantly increase the detection distance of the weak heartbeat signal. The successfully demonstrated detection distance for heartbeat is at least 250 cm, more than double the distance of the unlocked system. In addition, experiments were conducted to demonstrate effective measurements of vital sign in four physical orientations.

CONCLUSION

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. The patentable scope of certain embodiments of the disclosed technology is indicated by the appended claims, rather than the foregoing description, and all changes that come within the meaning and range of equivalents thereof are intended to be embraced therein.

What is claimed is:

1. A non-contact signal detection system comprising:
a noise pre-cancellation system configured to transmit a noise pre-cancelled signal; and
a controlled oscillation system configured to receive a first carrier signal, a second carrier signal, and the noise pre-cancelled signal, the controlled oscillation system comprising:
a modulator configured to frequency-modulate the first carrier signal and the second carrier signal with the noise pre-cancelled signal to produce frequency-modulated first and second carrier signals and wirelessly transmit a transmission signal comprising the frequency-modulated first and second carrier signals; and
a demodulator configured to receive the transmission signal, wherein the transmission signal is phase-modulated with a vibratory signal.

2. The non-contact signal detection system of claim 1 further comprising a carrier source configured to generate the first and second carrier signals;
wherein the carrier source is phase-locked to a first reference signal to establish phase coherence between the first carrier signal and the second carrier signal.

3. The non-contact signal detection system of claim 2, wherein the carrier source is in communication with a first branch including the first carrier signal power-combined with the second carrier signal, and a second branch including the second carrier signal.

4. The non-contact signal detection system of claim 3, wherein the first branch is in communication with the modulator and the second branch is in communication with the demodulator.

5. The non-contact signal detection system of claim 2 further comprising a low noise reference oscillator configured to generate the first reference signal.

6. The non-contact signal detection system of claim 1, wherein the noise pre-cancellation system comprises:
a phase-frequency detector;
a voltage controlled oscillator (VCO); and
a low-pass filter;
wherein the phase-frequency detector is configured to receive a beat signal from the demodulator and a second reference signal and is further configured to phase-lock the beat signal to the second reference signal to stabilize the phase of the beat signal; and
wherein the VCO is configured to pre-cancel noise associated with the phase-locked beat signal to transmit the noise pre-canceled signal.

7. The non-contact signal detection system of claim 4, wherein the transmission signal is transmitted to a third branch in communication with and between the modulator and the demodulator to provide auxiliary feedback to the demodulator.

8. The non-contact signal detection system of claim 6, wherein the demodulator is configured to extract the beat signal from the second carrier signal and transmit the beat signal to the phase-frequency detector of the noise pre-cancellation system.

9. The non-contact signal detection system of claim 1, wherein the demodulator is in communication with a data acquisition device configured to acquire information associated with the movement of the subject from the first carrier signal.

10. The non-contact signal detection system of claim 1, wherein:
the noise pre-cancellation system transmits the noise pre-cancelled signal;
the controlled oscillation system receives the first carrier signal, the second carrier signal, and the noise pre-cancelled signal;
the modulator frequency-modulates the first carrier signal and the second carrier signal with the noise pre-cancelled signal to produce the frequency-modulated first and second carrier signals;
the modulator wirelessly transmits the transmission signal;
the demodulator receives the transmission signal;
the noise pre-cancellation system comprises:
a phase-frequency detector;
a voltage controlled oscillator (VCO); and
a low-pass filter;
the phase-frequency detector phase-locks a beat signal to a second reference signal to stabilize the phase of the beat signal; and
the VCO pre-cancels noise associated with the phase-locked beat signal and transmits a noise pre-canceled signal to the controlled oscillation system.

11. The non-contact signal detection system of claim 1 further comprising a noise pre-cancellation system in communication with the oscillation system:
wherein the oscillation system comprises:
a modulator in communication with the noise pre-cancellation system and the carrier source and configured to frequency-modulate the first carrier signal and the second carrier signal with a noise pre-cancelled signal from the noise pre-cancellation system and transmit the first and second carrier signals to the subject.

12. The non-contact signal detection system of claim 11, wherein the receiver comprises a demodulator in communication with the carrier signal, the demodulator configured to frequency demodulate the first and second carrier signals.

13. The non-contact signal detection system of claim 12, wherein the demodulator is further configured to extract a beat signal from the second carrier signal and transmit the beat signal to the noise pre-cancellation system.

14. The non-contact signal detection system of claim 13, wherein the demodulator is in communication with a data acquisition device configured to extract the vibratory signal from the first carrier signal.

* * * * *